US012752219B2

(12) United States Patent
Polasek et al.

(10) Patent No.: US 12,752,219 B2
(45) Date of Patent: Oct. 6, 2026

(54) TETRAAZADODECANE BASED CHELATING AGENTS FOR SEPARATION OF RARE EARTH ELEMENTS AND METHOD THEREFOR

(71) Applicant: Ustav Organicke Chemie a Biochemie AV CR V.V.I., Prague (CZ)

(72) Inventors: Miloslav Polasek, Prague (CZ); Kelsea Grace Jones, Avon, NY (US); Tomas David, Hovorcovice (CZ)

(73) Assignee: Ustav Organicke Chemie a Biochemie AV CR V.V.I, Prague (CZ)

(*) Notice: Subject to any disclaimer, the term of this patent is extended or adjusted under 35 U.S.C. 154(b) by 617 days.

(21) Appl. No.: 18/027,283

(22) PCT Filed: Nov. 12, 2021

(86) PCT No.: PCT/CZ2021/050131

§ 371 (c)(1),
(2) Date: Mar. 20, 2023

(87) PCT Pub. No.: WO2022/100769

PCT Pub. Date: May 19, 2022

(65) Prior Publication Data

US 2023/0356105 A1 Nov. 9, 2023

(30) Foreign Application Priority Data

Nov. 13, 2020 (CZ) ................................ CZ2020-613

(51) Int. Cl.

*B01D 9/00* (2006.01)
*B01D 15/32* (2006.01)

(Continued)

(52) U.S. Cl.

CPC ........... *B01D 9/005* (2013.01); *B01D 15/327* (2013.01); *B01D 61/145* (2013.01); *C01F 17/13* (2020.01);

(Continued)

(58) Field of Classification Search

CPC .... B01D 9/005; B01D 15/327; B01D 61/145; B01D 2009/0086; B01D 9/00;

(Continued)

(56) References Cited

U.S. PATENT DOCUMENTS

| | | | | |
|---|---|---|---|---|
| 2,943,101 A * | 6/1960 | Kurt | C22B 59/00 | 556/139 |
| 3,252,754 A * | 5/1966 | Kraitzer | C22B 59/00 | 423/17 |

(Continued)

FOREIGN PATENT DOCUMENTS

| | | |
|---|---|---|
| EP | 3492460 A1 | 6/2019 |
| JP | 2009529501 A | 8/2009 |

(Continued)

OTHER PUBLICATIONS

Faulkner, Stephen, et al; "pH Dependent self-assembly of dimetallic lanthanide complexes"; Chemical Communications; Nov. 19, 2004; 2:259-261.

(Continued)

*Primary Examiner* — Cam N. Nguyen
(74) *Attorney, Agent, or Firm* — Notaro, Michalos & Zaccaria P.C.

(57) ABSTRACT

Compounds of general formula (I) for separations of rare earth elements (lanthanides) by precipitation are discussed, where R1 is selected from the group consisting of H; —CH2COOH; R2, R3, R4, R5 and R6 are independently selected from the group consisting of H; OH; —NO2;

(Continued)

—COOH; phenyl; and/or R2 and R3 or R3 and R4 or R4 and R5, or R5 and R6 together with two neighbouring carbon atoms of the aromatic ring form a six-membered aromatic ring. Also discussed is a method of separation of rare earth elements by precipitation.

(I)

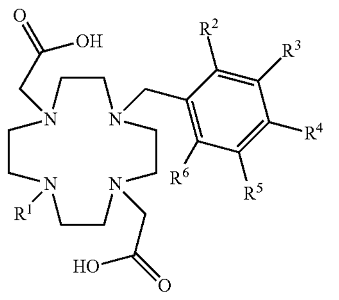

18 Claims, 1 Drawing Sheet

(51) Int. Cl.

| | |
|---|---|
| ***B01D 61/14*** | (2006.01) |
| ***C01F 17/13*** | (2020.01) |
| ***C01F 17/271*** | (2020.01) |
| ***C07D 257/02*** | (2006.01) |
| ***C22B 59/00*** | (2006.01) |

(52) U.S. Cl.
CPC ............ *C07D 257/02* (2013.01); *C22B 59/00* (2013.01); *B01D 2009/0086* (2013.01)

(58) Field of Classification Search
CPC ...... C01F 17/13; C01F 17/271; C07D 257/02; C22B 59/00; Y02P 10/20; Y02W 30/20; Y02W 30/82
USPC ........................................................ 423/21.5
See application file for complete search history.

(56) References Cited

U.S. PATENT DOCUMENTS 3,402,047 A * 9/1968 Shaul ...................... C12H 6/04 62/541
5,129,945 A * 7/1992 Lyman ................. C01F 17/265 75/416
8,198,101 B2 6/2012 Kovacs et al.
8,518,715 B2 8/2013 Kovacs et al.
9,376,735 B2 * 6/2016 Jacobson .................. B09B 3/70
10,196,709 B2 * 2/2019 Jacobson .................. C22B 3/22
10,689,727 B2 * 6/2020 Freiderich ............... C22B 3/286
10,787,722 B2 * 9/2020 Seisenbaeva ........... C22B 7/007
11,091,819 B2 * 8/2021 Kasaini ..................... C22B 3/44
11,186,894 B2 * 11/2021 Wang ...................... C01G 49/10
11,345,977 B2 * 5/2022 Kasaini ............... C22B 60/0291
11,396,684 B2 * 7/2022 Nockemann ............ C22B 59/00
11,761,058 B2 * 9/2023 Li ............................. D01F 1/02 208/428
12,398,444 B2 * 8/2025 Jansone-Popova ..... C22B 3/282

FOREIGN PATENT DOCUMENTS

| | | | |
|---|---|---|---|
| JP | 2013253311 | A | 12/2013 |
| JP | 2015078396 | A | 4/2015 |
| WO | 2007104135 | A1 | 9/2007 |
| WO | WO2019106182 | A1 | 6/2019 |
| WO | WO2020244686 | A1 | 12/2020 |
| WO | WO2020259726 | A1 | 12/2020 |

OTHER PUBLICATIONS

Baranyai, Zsolt, et al; “The Use of the Macrocyclic Chelator DOTA in Radiochemical Separations”; European Journal of Inorganic Chemistry; Nov. 25, 2019; 2020(1):36-56.
Krishan, Kumar, et al; “Equilibrium and kinetic studies of lanthanide complexes of macrocyclic polyamino carboxylates”; Inorganic Chemistry; Mar. 1, 1993; 32(5):587-593.
Bogart, Justin A., et al; “An Operationally Simple Method for Separating the Rare-Earth Elements Neodymium and Dysprosium”; Angewandte Chemie International Edition; May 26, 2015; 54(28):8222-8225.
Bogart, Justin A., et al; “Accomplishing simple, solubility-based separations of rare earth elements with complexes bearing size-sensitive molecular apertures”; Proceedings of the National Academy of Sciences; Dec. 12, 2016; 113(52):14887-14892.
International Search Report and Written Opinion for PCT Application No. PCT/CZ2021/050131, mailed Mar. 1, 2022.
International Preliminary Report on Patentability, completed Oct. 25, 2022.
Demand/Request for Preliminary Examination dated Sep. 5, 2022.
Response to Written Opinion of International Searching Authority dated Sep. 5, 2022.
International Application Status Report generated Mar. 1, 2023.
Japanese Notice of Reasons for Refusal, prepared Jul. 26, 2024.
Regueiro-Figueroa, M.; Esteban-Gómez, D.; de Blas, A.; Rodríguez-Blas, T.; Platas-Iglesias, C “Structure and Dynamics of Lanthanide(III) Complexes with an N-Alkylated Do3a Ligand (H3do3a = 1,4,7,10-Tetraazacyclododecane-1,4,7-Triacetic Acid): A Combined Experimental and DFT Study” Eur. J. Inorg. Chem. 2010, 2010 (23), 3586-3595.

* cited by examiner

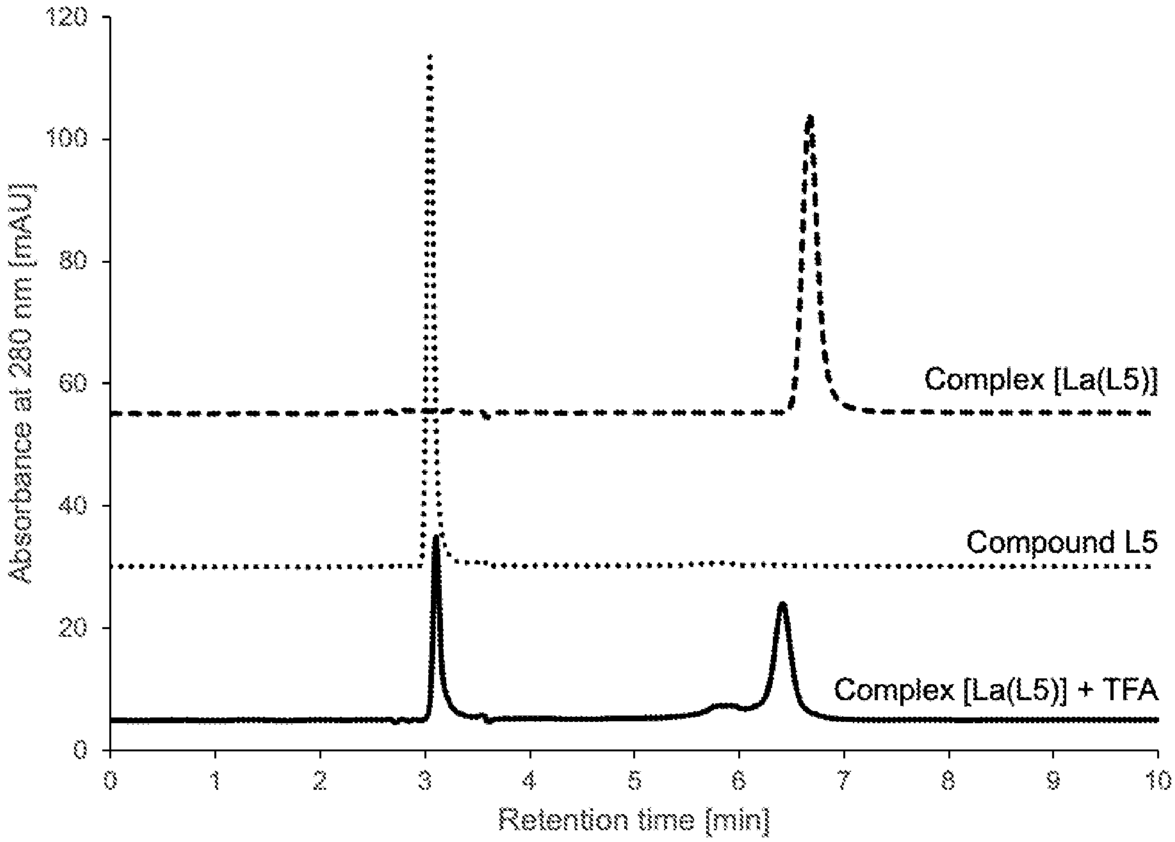
Absorbance at 280 nm [mAU]
120
100
80
60
40
20
0
Complex [La(L5)]
Compound L5
Complex [La(L5)] + TFA
0
1
2
3
4
5
6
7
8
9
10
Retention time [min]

TETRAAZADODECANE BASED CHELATING AGENTS FOR SEPARATION OF RARE EARTH ELEMENTS AND METHOD THEREFOR

TECHNICAL FIELD

This invention relates to cyclen based compounds suitable for extraction and separation of rare earth elements, for example from discarded electronic and electric equipment based on different solubilities, and to a method of separating the rare earth elements.

BACKGROUND ART

Rare earth elements (scandium—Sc, yttrium—Y, lanthanum—La, cerium—Ce, praseodymium—Pr, neodymium—Nd, promethium—Pm, samarium—Sm, europium—Eu, gadolinium—Gd, terbium—Tb, dysprosium—Dy, holmium—Ho, erbium—Er, thulium—Tm, ytterbium—Yb and lutetium—Lu) are metals with very similar chemical properties. These elements are indispensable in a number of modern technologies. Nd and Dy are crucial for strong permanent magnets that are used in electric motors, wind turbines and computer hard drives. Eu, Tb and Y are important components in luminescent phosphors in fluorescent lamps. Ce and Y are used in the currently most advanced lighting technology of light emitting diodes (LED). It is expected that the number of industrial applications of rare earth elements will grow and so will their overall consumption. However, extraction of these elements from primary ores is problematic. Firstly, majority of global production is coming from a single country—China. For this reason, European Union and USA have placed some rare earth elements on the list of critical raw materials. Secondly, ore processing and purification of individual elements to the degree suitable for the applications mentioned above are energetically demanding and produce high amounts of toxic and radioactive waste. An obvious solution is to recycle rare earth elements from discarded equipment and electronic waste, which are generated in large quantities each year by the developed world. Despite this, only a few percent of previously used rare earth elements is currently recycled. While separation of rare earth elements from other metals with sufficiently different properties is a solved problem, separation of rare earth elements from each other remains technologically and financially demanding. For these reasons, rare earth element recycling does not pay off.

Historically, rare earth elements have been separated from each other by fractional crystallizations that required thousands of repetitions to obtain pure products. Current industrial methods rely mainly on solvent-solvent extraction, and for high purity on smaller scale ion-exchange chromatography. None of these methods is selective for specific elements. Only the solvent-solvent extraction provides the capacity to cover the industrial demand. However, this method has several drawbacks. The requirement for series of hundreds of extractors represents a large infrastructure with high investment and operations cost. Moreover, this method requires use of water-immiscible solvents and extractants harmful to the environment. Development of alternative methods that would be simpler, more selective and environmentally friendly is very desirable.

Precipitation and crystallization are purification methods preferred in industry for their simplicity, efficiency and scalability to large quantities. Using these methods for separation of rare earth elements would be very advantageous. However, the problem is to find chemical agents that would cause a sufficient difference in solubility between these elements. In recent years, several works have demonstrated some advancements in this field. Chelating ligands have been used for separation of rare earth elements based on different solubilities of their complexes in tetrahydrofuran. (Bogart, J. A. et al. *Angew. Chem.* 2015, 127, 8340-8343 a Bogart, J. A. et al. *PNAS* 2016, 113, 14887-14892). Light elements (La—Eu) were efficiently separated from the heavy elements (Gd—Lu), but separation of two neighboring lanthanides was not demonstrated. A disadvantage of the method was the necessity to use organic solvents, such as tetrahydrofuran, benzene or toluene, which are toxic and unecological.

Another work demonstrated the possibility to separate rare earth elements using hydrothermal synthesis of crystalline borates differing in crystal structure. (Yin, X. et al. *Nat. Commun.* 2017, 8:14438). The separation was achieved between the aqueous solution and solid phase, or between two crystalline solid phases that could be separated based on different crystal densities. However, the reaction conditions for the synthesis were quite demanding, requiring use of autoclave, temperature of 200° C., and long crystallization times of 3 to 5 days. Moreover, even in this case, effective separation of two neighboring lanthanides was not demonstrated.

Yet another work showed selective precipitation of insoluble hydroxides of lanthanides from aqueous solutions with the help of specially designed peptides. (Hatanaka, T. et al. *Nat. Commun.* 2017, 8:15670). Some of the peptides showed selectivity for precipitation of heavy lanthanides in comparison with lighter lanthanides. The separation of two neighboring lanthanides was not studied.

The background art thus lacks a method suitable for separation of rare earth elements that would be simple, efficient, scalable to large quantities, and simultaneously would not require use of toxic and unecological solvents or expensive equipment or high temperatures and pressures.

DISCLOSURE OF INVENTION

Chelators structurally derived from macrocyclic cyclen (1,4,7,10-tetraazacyclododecane) are especially suitable for complexation of rare earth elements. In the background art, a large number of such chelators was prepared and studied for use in biomedical applications. Complexes of gadolinium serve as contrast agents in magnetic resonance tomography, complexes with radionuclides $^{90}Y$ and $^{177}Lu$ are used in targeted drugs for treatment of cancer. For all these uses, it is desirable that the complexes are highly stable and soluble in water. In contrast to this is our surprising finding that some chelators derived from cyclen show significant differences in solubility of complexes with different rare earth elements. These differences are sufficiently large to be practically usable for separation of these elements from each other. The separation is carried out by precipitation from aqueous solutions of mixtures of elements and does not necessarily require use of organic solvents. The separated solid phase can be re-dissolved and the precipitation step can be repeated to reach higher degree of separation. The separated solid complex can be decomposed back to the free chelator and a rare earth metal cation for next use. The mother liquor may also be used after its thickening and/or ultrafiltration and/or ion-exchange chromatography to precipitate and separate the solid complex of rare earth elements. Thus, this method of separation solves the problems of background art mentioned above, because it is very efficient, easy, ecological, and scalable to industrial scale. Moreover, it does not require any special and expensive instrumentation.

The object of the present invention is the use of compounds of general formula (I)

(I)

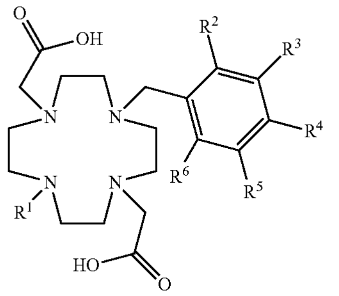

for separations of rare earth elements (lanthanides) by precipitation, wherein $R^1$ is selected from the group consisting of H; —$CH_2COOH$;

$R^2$, $R^3$, $R^4$, $R^5$ and $R^6$ are independently selected from the group consisting of H; OH; —$NO_2$; —COOH; phenyl;

and/or $R^2$ and $R^3$ together with two neighbouring carbon atoms of the aromatic ring form a six-membered aromatic ring;

and/or $R^3$ and $R^4$ together with two neighbouring carbon atoms of the aromatic ring form a six-membered aromatic ring;

and/or $R^4$ and $R^5$ together with two neighbouring carbon atoms of the aromatic ring form a six-membered aromatic ring;

and/or $R^5$ and $R^6$ together with two neighbouring carbon atoms of the aromatic ring form a six-membered aromatic ring.

Compounds of the general formula (I) form coordination compounds (complexes) with rare earth elements, and these coordination compounds considerably differ in their water solubility. It is therefore possible to separate them by precipitation.

By the term "precipitation" it is meant exclusion of a compound in solid phase from a solution. The solid phase may be in a form of a precipitate or in crystalline form.

The rare earth elements are selected from scandium—Sc, yttrium—Y, lanthanum—La, cerium—Ce, praseodymium—Pr, neodymium—Nd, promethium—Pm, samarium—Sm, europium—Eu, gadolinium—Gd, terbium—Tb, dysprosium—Dy, holmium—Ho, erbium—Er, thulium—Tm, ytterbium—Yb and lutecium—Lu.

In one preferred embodiment, at most two of the substituents $R^2$, $R^3$, $R^4$, $R^5$ and $R^6$ are other than H.

In one preferred embodiment, one of the substituents $R^2$, $R^3$, $R^4$, $R^5$ and $R^6$ is other than H.

In one embodiment, $R^2$ and $R^6$ are independently H or OH.

In one embodiment, $R^3$ and $R^4$ together with two neighbouring carbon atoms of the aromatic ring form a six-membered aromatic ring and at the same time $R^2$, $R^5$ and $R^6$ are H.

In one embodiment, $R^2$, $R^3$, $R^4$, $R^5$ and $R^6$ are H.

In one embodiment, the group

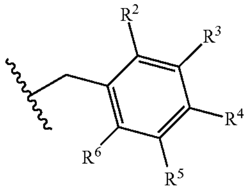

of the general formula (I) is selected from the group comprising naphtalen-1-ylmethyl, naphtalen-2-ylmethyl and benzyl.

In one embodiment, $R^2$, $R^3$, $R^5$ and $R^6$ are H, and $R^4$ is phenyl, H or COOH.

In the most preferred embodiment, the compound of general formula (I) is selected from the group consisting of:

2,2',2"-(10-benzyl-1,4,7,10-tetraazacyclododecane-1,4,7-triyl)triacetic acid;

2,2'-(4-(2-hydroxy-5-nitrobenzyl)-1,4,7,10-tetraazacyclododecane-1,7-diyl)diacetic acid;

2,2'-(4-(4-carboxybenzyl)-1,4,7,10-tetraazacyklododekane-1,7-diyl)diacetic acid;

2,2',2"-(10-(naphthalene-2-ylmethyl)-1,4,7,10-tetraazacyklododekane-1,4,7-triyl)triacetic acid;

2,2',2"-(10-(naphthalene-1-ylmethyl)-1,4,7,10-tetraazacyklododekane-1,4,7-triyl)triacetic acid;

2,2',2"-(10-([1,1'-biphenyl]-4-ylmethyl)-1,4,7,10-tetraazacyclododecane-1,4,7-triyl)triacetic acid.

Further object of the present invention is a method of separation of rare earth elements by precipitation. This method comprises the following steps:

o) Providing aqueous solution of ions of at least two different rare earth elements ($M^{3+}$) to be separated, and aqueous solution of the compound of general formula (I) defined above;

a) Reaction of aqueous solution of ions of at least two different rare earth elements ($M^{3+}$) to be separated with aqueous solution of the compound of general formula (I) defined above; pH of the resulting solution is preferably in the range of from 5 to 9, more preferably in the range of from 6 to 8; resulting in formation of complexes of the $M^{3+}$ ions with the compound of general formula (I), wherein at least one of the complexes formed is in the form of a precipitate or a crystal phase (therefore a heterogenous mixture is formed, containing at least one of the complexes in solid form, while the solution is enriched by the more soluble complex).

Most preferably, the step a) takes place at pH 7.

Preferably, step a) takes place at constant stirring or shaking

The solubility (in water or in the reaction mixture, respectively) of the resulting complex of the compound of general formula (I) with the metal cation $M^{3+}$ differs for various rare earth metal ions.

For this reason, the precipitation occurs preferentially only with one of the metal ions to be separated, present in the reaction mixture. Complexes of the remaining rare earth metal ion(s) with the compound of the general formula (I) stay dissolved in the reaction mixture.

For some combinations of more than two rare earth metal cations to be separated, it may be that more than one complex of the compound of general formula (I) with the metal cation $M^{3+}$ are precipitated or crystallized from the reaction mixture. For example, an aqueous solution of four rare earth metal cations may upon complexation with the compound of general formula (I) lead to precipitation of two of the complexes formed, leaving the remaining two complexes in the solution mixture.

In every case, the reaction mixture is enriched by the more soluble complex or complexes.

Preferably, step a) takes place for at least 1 minute, more preferably from 1 minute to 5 days.

Preferably, step a) takes place at room temperature (20 to 25° C.).

Aqueous solution is a solution, wherein the solvent is selected from the group comprising water, buffer (for example MOPS, 3-(N-morpholino)propanesulfonic acid) and/or a mixture of water and organic solvent, which is miscible with water.

In cases where the solvent is a mixture of water and organic solvent, which is miscible with water, the preferable water content is at least 50 vol. %, more preferably the water content is from 60 to 95 vol. %, even more preferably from 70 to 85 vol. %.

The organic solvent, which is miscible with water, may be for example acetonitrile, dimethylsulfoxide, N,N-dimethylformamide or (C1 to C4) alcohol, preferably acetonitrile, methanol and/or ethanol.

The starting aqueous solution of the compound of the general formula (I) can be obtained by dissolving of the previously prepared compound of general formula (I) in water, buffer and/or a mixture of water and organic solvent, which is miscible with water.

The starting aqueous solution of ions of at least two different rare earth metals ($M^{3+}$) is preferably obtained by recycling discarded electronic and electric equipment, for example dissolving neodymium magnets in sulfuric acid or in nitric acid, or combustion of neodymium magnets, followed by their dissolution in sulfuric, nitric or hydrochloride acid. Another example may be dissolving of luminescent materials from fluorescent lamps in sulfuric, nitric or hydrochloride acid, or in mixture thereof, or in a mixture of HCl and hydrogen peroxide.

Preferably, the total molar concentration of all $M^{3+}$ ions in the reaction mixture in step a) is in the range of from 0.0001 to 1 mol/L, more preferably from 0.001 to 0.1 mol/L, most preferably in the range of from 0.005 to 0.05 mol/L.

In a preferred embodiment, the molar ratio between the sum of rare earth metal ions and the compound of the general formula (I) is in the range of from 1:0.5 to 1:100.

b) Mechanical separation of the precipitate or of the crystalline phase from the reaction mixture, preferably using sedimentation, centrifugation or filtration.

Methods for separating heterogeneous mixtures, comprising solid and liquid phase, are known to the skilled person.

The result of step b) is the solid complex of $M^{3+}$ ion or a mixture of solid complexes of $M^{3+}$ ions with the compound of general formula (I), which may further undergo the optional steps c) and d). The remaining complexes of rare earth metal cation(s), which did not precipitate/crystallize, stay dissolved in the reaction mixture/mother liquor/filtrate/supernatant solution, from which the solid phase has been separated. In summary, the chemical equilibrium of the insoluble complexes is driven by their precipitation/crystallization, while the reaction mixture/mother liquor is enriched by the soluble complexes.

c) Optionally, re-dissolving of the precipitate or of the crystalline phase from step b) in water, buffer, a mixture of water and organic solvent, which is miscible with water, or in aqueous solution of inorganic or organic acid such as HCl or trifluoroacetic acid (pH in the range of from 0 to 4), preferably in aqueous HCl.

More preferably, this step may be performed at the temperature of at least 30° C., even more preferably at the temperature in the range of from 40 to 100° C. In this step, the solid complex is re-dissolved and/or hydrolyzed into free compound of general formula (I) and $M^{3+}$ cation.

d) Optionally, pH adjustment of the solution from step c) to the pH value in the range of from 5 to 9 (for example by using aqueous NaOH), and repeating of steps a), b) and optionally c). By repeating of the separation cycle, a higher degree of separation of rare earth metals M can be achieved. In one embodiment, compound of the general formula (I) may be separated from the reaction mixture after dissolving the precipitate or crystalline phase in step c). (Meaning after hydrolysis of the particular complex.) The separation of the compound of the general formula (I) can be performed using for example solid phase extraction (SPE), or by chromatography (e.g. normal or reverse phase chromatography, ion-exchange chromatography), or using sorption on activated carbon. The remaining solution thus contains only pure water-soluble salt of the separated rare earth metal cation.

In one preferred embodiment, the aqueous solution of ions of at least two different rare earth elements ($M^{3+}$) in step a) contains their water-soluble salts with inorganic or organic acids, preferably selected from the group comprising chloride, bromide, sulfate, nitrate, perchlorate, methanesulfonate, trifluoromethanesulfonate, formate, acetate, lactate, malate, citrate, 2-hydroxyisobutyrate, mandelate, diglycolate and/or tartrate.

Water-soluble salt is understood to have solubility in water at 25° C. of at least 0.5 g/100 ml of water.

In one aspect of the invention, additives may be used to improve the separation of rare-earth elements. The additives are selected from the group comprising carboxylic acids comprising from 1 to 11 carbon atoms (comprising at least one carboxylic group and a (C1 to C10) linear or branched hydrocarbon chain and/or (C6-C10)aryl moiety), phosphinic acids comprising from 1 to 10 carbon atoms (comprising (C1 to C10) linear or branched hydrocarbon chain and/or (C6-C10)aryl moiety), phosphonic acids comprising from 1 to 10 carbon atoms (comprising (C1 to C10) linear or branched hydrocarbon chain and/or (C6-C10)aryl moiety), trifluoroacetic acid, 3-chlorobenzoic acid, chloride; dipicolinic acid, fluoride, glycine, glycolate, α-HIBA (alpha-hydroxyisobutyric acid), lactate, nitrate, phenylboronic acid, picolinic acid, pyridine, mandelic acid, salicylic acid, sulfate, thiocyanate, tributyl phosphate, dimethylsulfoxide, N,N-dimethylformamide, N,N-dimethylacetamide; preferably the additive is selected from the group comprising acetate, trifluoroacetic acid, benzoic acid, 3-chlorobenzoic acid, 2-methylbenzoic acid, 3-methylbenzoic acid, 4-methylbenzoic acid, chloride, citrate, dipicolinic acid, fluoride, formate, glycine, glycolate, α-HIBA (alpha-hydroxyisobutyric acid), lactate, nitrate, phenylboronic acid, picolinic acid, pyridine, mandelic acid, salicylic acid, sulfate, thiocyanate, tributyl phosphate, dimethylsulfoxide, N,N-dimethylformamide, N,N-dimethylacetamide. Preferably, sodium or potassium salts of the additives are used. In the case of chiral centers in the molecule, the list of additives also includes optically active isomers, mixtures thereof and racemates.

It has been observed that the presence of an additive increases the solubility of heavier rare earth metal complexes with the compounds of general formula (I), thus keeping them in solution, while the lighter rare earth metal complexes with the compounds of general formula (I) precipitate/crystallize because they are less affected by the presence of the additive. In other words, the additives in general increase the solubility of rare earth metal complexes with compounds of general formula (I), however their effect is relative as they enhance more the solubility of heavier rare earth metal complexes with the compounds of general formula (I). It results in a greater solubility difference between a lighter rare earth metal complex and a heavier rare earth metal complex. It is to be understood that the mass of the complexes continuously increases along the lanthanide series (from La to Lu), thus the presence of the additive usually increases more the solubility of a complex with rare earth element of higher proton number than of a complex with rare earth element of lower proton number. As a result, the efficiency of the separation is greatly enhanced by using the additives.

The aqueous solution of at least one additive (preferably having pH in the range of from 6 to 8, more preferably of pH 7) is added to the reaction mixture in step a) of the method of separation described above.

In one preferred embodiment, the molar ratio between the sum of rare earth metal ions and the additive in the reaction mixture in step a) is in the range of from 1:0.1 to 1:100, more preferably from 1:0.5 to 1:50, even more preferably from 1:1 to 1:10.

Use of the additive in step a) greatly and unexpectedly increases the separation factor.

In one embodiment, after precipitation of the complex has occurred (step b)), the additive may be removed from the reaction mixture, preferably using HPLC or ultrafiltration (e.g. using an ultrafiltration system with a membrane for nanofiltration) or ion-exchange chromatography.

The rare earth metal complexes present in the reaction mixture/mother liquor/filtrate/supernatant solution, from which the solid phase has been separated in step b), may further undergo an optional step e), in which the reaction mixture/mother liquor/filtrate/supernatant solution from step b) is subjected to evaporation and/or ultrafiltration and/or ion-exchange chromatography. Thereby the concentration of the rare earth metal complexes with the compound of general formula (I) in the solution increases and/or the concentration of additives decreases, causing the metal complex(es) to precipitate or crystallize.

The ultrafiltration is preferred because it simultaneously removes the additives from the solution and increases the concentration of the metal complexes. Removal of the additives from the solution not only purifies the mixture but also shifts the precipitation equilibrium of the dissolved rare earth metal complexes towards precipitation, so even more precipitated/crystallized complex can be obtained.

BRIEF DESCRIPTION OF DRAWINGS

FIG. 1: HPLC chromatograms discussed in Example 28. From top to the bottom: complex [La(L5)], free compound L5 and complex [La(L5)] after partial decomposition in TFA.

EXAMPLES

I. Compound Synthesis

Structures of commercially available synthetic precursors A and B

A

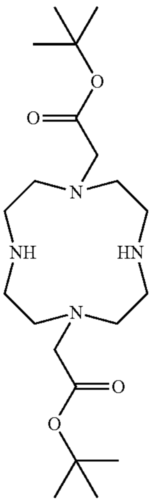

B

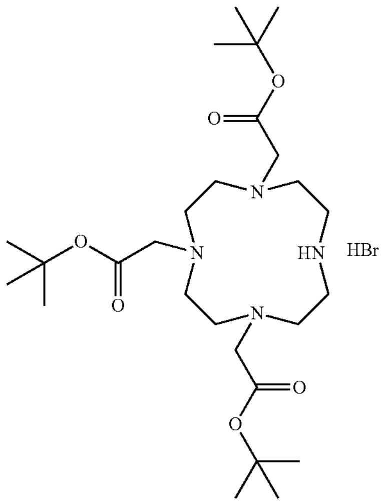

Example 1) Synthesis of 2,2',2"-(10-benzyl-1,4,7,10-tetraazacyclododecane-1,4,7-triyl)triacetic Acid (L1)

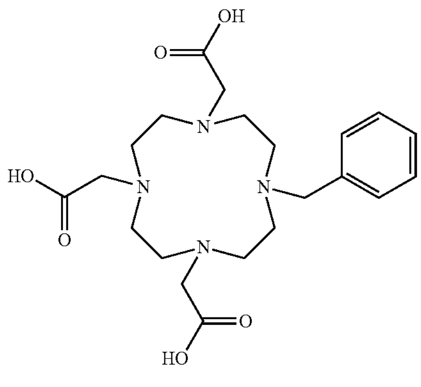 [SMILES: O=C(O)CN1CCN(CC(=O)O)CCN(Cc2ccccc2)CCN(CC(=O)O)CC1]

Starting material B (1.00 g, 1.68 mmol), benzyl bromide (302 mg, 1.76 mmol), anhydrous potassium carbonate (1.16 g, 8.39 mmol) and acetonitrile (50 mL) were mixed in a 100 mL round-bottom flask equipped with a magnetic stir bar. The flask was capped and the mixture was stirred on a magnetic stirrer at room temperature for 48 hours. Then the mixture was filtered through a glass frit and the filtrate was concentrated by rotary evaporation. The resulting oily compound was purified using preparative HPLC (C18 reverse-phase column, acetonitrile/water gradient with 0.1% TFA (trifluoroacetic acid) in mobile phase). Fractions containing product in the form of the tert-butyl ester were collected, concentrated by rotary evaporation, and further dried under high vacuum. This oily product was dissolved in TFA (10 mL) and left stiffing at room temperature for 24 hours. After that, the TFA was removed by rotary evaporation and the residue was purified using preparative HPLC (C18 reverse phase-column, acetonitrile/water gradient with 0.1% TFA in mobile phase). Fractions containing product were collected, concentrated by rotary evaporation, re-dissolved in 5 mL of water, and lyophilized. The final yield was 304 mg of L1 as a white powder (0.507 mmol, yield 30% based on precursor B).

HRMS (ESI) m/z: $[(M+H)^+]$ ($C_{21}H_{33}N_4O_6$) calculated: 437.2395, found: 437.2392.

Elemental analysis: M·2.1TFA·1.1$H_2O$, calculated: C (43.5), H (5.3), N (8.1), F (17.2), found: C (43.6), H (5.0), N (7.8), F (17.3).

Example 2) Synthesis of 2,2'(4-(2-hydroxy-5-nitrobenzyl)-1,4,7,10-tetraazacyclododecane-1,7-diyl) Diacetic Acid (L2)

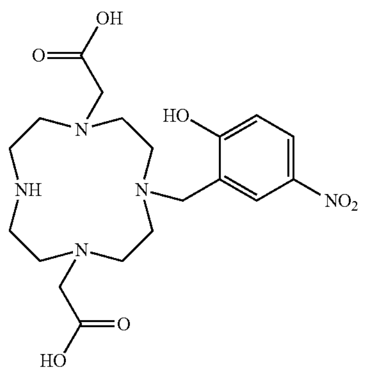 [SMILES: O=C(O)CN1CCNCCN(CC(=O)O)CCN(Cc2cc([N+](=O)[O-])ccc2O)CC1]

Starting material A (2.00 g, 4.99 mmol) was dissolved in acetonitrile (25 mL). A solution of 2-(bromomethyl)-4-nitrophenol (579 mg, 2.50 mmol) in acetonitrile (100 mL) was slowly added dropwise over the course of 2 hours while stiffing at room temperature. The reaction was stirred at room temperature for another 24 hours. The mixture was then concentrated by rotary evaporation. The resulting oily compound was purified by preparative HPLC (C18 reverse phase column, acetonitrile/water gradient with 0.1% TFA in mobile phase). Starting material A and doubly-alkylated byproduct were both removed in this step. Fractions containing product in the form of tert-butyl ester were joined, concentrated by rotary evaporation, and further dried under high vacuum. This oily product was dissolved in TFA (10 mL) and left stiffing at room temperature for 24 hours. After that, the TFA was removed by rotary evaporation and the residue was purified using preparative HPLC (C18 reverse-phase column, gradient acetonitrile/water with 0.1% TFA in mobile phase). Fractions containing product were collected, concentrated by rotary evaporation, re-dissolved in 5 mL of water, and lyophilized. The final yield was 935 mg of L2 as a pale-yellow powder (1.32 mmol, yield 35% based on 2-(bromomethyl)-4-nitrophenol).

HRMS (ESI) m/z: $[(M+H)^+]$ ($C_{19}H_{30}N_5O_7$) calculated: 440.2140, found: 440.2138.

Elemental analysis: M·2.35TFA, calculated: C (40.2), H (4.5), N (9.9), F (18.9), found: C (40.3), H (4.5), N (9.7), F (19.2).

Example 3) Synthesis of 2,2'-(4-(4-carboxybenzyl)-1,4,7,10-tetraazacyklododekane-1,7-diyl)Diacetic Acid (L3)

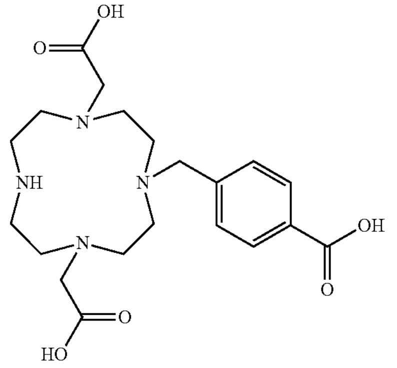 [SMILES: O=C(O)CN1CCNCCN(CC(=O)O)CCN(Cc2ccc(C(=O)O)cc2)CC1]

Starting material A (2 g, 4.99 mmol) was dissolved in acetonitrile (25 mL). A solution of 4-(bromomethyl)benzoate (614 mg, 2.85 mmol) in acetonitrile (100 mL) was slowly added dropwise over the course of 2 hours while stirring at room temperature. The reaction was stirred at room temperature for another 24 hours. The mixture was then concentrated by rotary evaporation. The resulting oily compound was purified by preparative HPLC (C18 reverse-phase column, acetonitrile/water gradient with 0.1% TFA in mobile phase). Starting material A and doubly-alkylated byproduct were both removed in this step. Fractions containing product in the form of tert-butyl ester were collected and concentrated by rotary evaporation. The resulting oil was dissolved in methanol (25 mL). Lithium hydroxide monohydrate (290 mg, 6.91 mmol) was dissolved in water (25 mL) and added to the reaction mixture. The reaction mixture was stirred 4 hours at room temperature. The reaction was then stopped by addition of TFA (787 mg, 6.91 mmol) and concentrated by rotary evaporation. The resulting oil was purified by preparative HPLC (C18 reverse-phase column, gradient acetonitrile/water with 0.1% TFA in mobile phase). Fractions containing partially protected product (2× tert-butyl ester, lx free carboxylic acid on benzyl group) were collected and concentrated by rotary evaporation. The resulting oil was dissolved in TFA (15 mL) and left stiffing at room temperature for 24 hours. After that, the TFA was removed by rotary evaporation and the product was purified using preparative HPLC (C18 reverse-phase column, acetonitrile/water gradient with 0.1% TFA in mobile phase). Fractions containing product were collected, concentrated by rotary evaporation, re-dissolved in 5 mL of water, and lyophilized. The final yield was 359 mg of L3 as a white powder (0.495 mmol, yield 17% based on 2-(bromomethyl)-benzoate).

HRMS (ESI) m/z: $[(M+H)^+]$ ($C_{20}H_{31}N_4O_6$) calculated: 423.2238, found: 423.2237.

Elemental analysis: M·2.65TFA, calculated: C (41.9), H (4.5), N (7.7), F (20.8), found: C (42.0), H (4.5), N (7.7), F (21.2).

Example 4) Synthesis of 2,2',2"-(10-(naphthalene-2-ylmethyl)-1,4,7,10-tetraazacyklododekane-1,4,7-triyl)triacetic acid (L4)

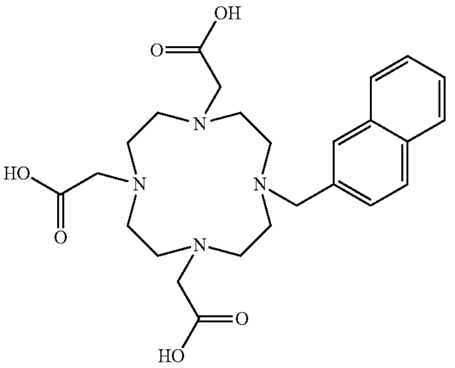 [SMILES: O=C(O)CN1CCN(CC(=O)O)CCN(Cc2ccc3ccccc3c2)CCN(CC(=O)O)CC1]

According to the procedure of Example 1), compound B (250 mg, 0.420 mmol), 2-(bromomethyl)naphthalene (97.4 mg, 0,441 mmol), anhydrous potassium carbonate (290 mg, 2.099 mmol), and acetonitrile (15 mL) were mixed and the reaction was processed analogously to the procedure described for Example 1. The final yield was 181.4 mg of L4 as a white powder (0.255 mmol, yield 61% based on precursor B).

HRMS (ESI) m/z: $[(M+H)^+]$ ($C_{25}H_{35}N_4O_6$) calculated: 487.2551, found: 487.2549.

Elemental analysis: M·1.8TFA·1.0$H_2O$, calculated: C (48.4), H (5.4), N (7.9), F (14.4), found: C (48.2), H (5.2), N (8.1), F (14.7).

Example 5) Synthesis of 2,2',2"-(10-(naphthalene-1-ylmethyl)-1,4,7,10-tetraazacyklododekane-1,4,7-triyl)triacetic acid (L5)

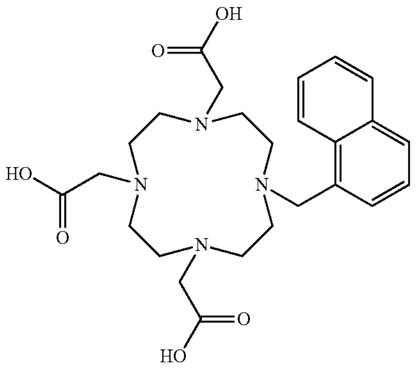 [SMILES: O=C(O)CN1CCN(CC(=O)O)CCN(Cc2cccc3ccccc23)CCN(CC(=O)O)CC1]

According to the procedure of Example 1), compound B (250 mg, 0.420 mmol), 1-(bromomethyl)naphthalene (97.4 mg, 0,441 mmol), anhydrous potassium carbonate (290 mg, 2.099 mmol), and acetonitrile (15 mL) were mixed and the reaction was processed analogously to the procedure described for Example 1). The final yield was 202.3 mg of L5 as a white powder (0.285 mmol, yield 68% based on precursor B).

HRMS (ESI) m/z: $[(M+H)^+]$ ($C_{25}H_{35}N_4O_6$) calculated: 487.2551, found: 487.2553.

Elemental analysis: M·1.75TFA·1.3$H_2O$, calculated: C (48.3), H (5.5), N (7.9), F (14.1), found: C (48.2), H (5.2), N (8.0), F (14.0).

Example 6) Synthesis of 2,2',2"-(10-([1,1'-biphenyl]-4-ylmethyl)-1,4,7,10-tetraazacyclododecane-1,4,7-triyl)triacetic acid (L6)

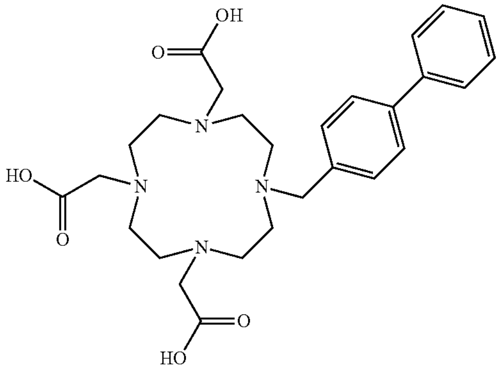 [SMILES: O=C(O)CN1CCN(CC(=O)O)CCN(Cc2ccc(-c3ccccc3)cc2)CCN(CC(=O)O)CC1]

According to the procedure of Example 1), compound B (300 mg, 0.50 mmol), 4-bromomethylbiphenyl (247.1 mg, 0.530 mmol), anhydrous potassium carbonate (348 mg, 2.52 mmol), and acetonitrile (18 mL) were mixed and the reaction was processed analogously to the procedure described for Example 1). The final yield was 285.2 mg of L6 as a white powder (0.385 mmol, yield 76% based on precursor B).

HRMS (ESI) m/z: $[(M+H)^+]$ ($C_{27}H_{37}N_4O_6$) calculated: 513.2713, found: 513.2710.

Elemental analysis: M·1.8TFA·1.25$H_2O$, calculated: C (49.7), H (5.5), N (7.6), F (13.9), found: C (49.9), H (5.1), N (7.3), F (13.5).

II. Separation of Rare-Earth Elements by Precipitation from Solutions

Example 7) Separation of Binary Mixture of Rare-Earth Metals by Precipitation from Solution Using L1

To the 96-well plate were pipetted stock solutions as follows:

1. 5 μL 100 mM aqueous solution of rare-earth element chloride number 1 (M1)
2. 5 μL 100 mM aqueous solution of rare-earth element chloride number 2 (M1)
3. 10 μL 100 mM aqueous solution of compound L1.
4. 20 μL 3 M MOPS (3-(N-morpholino)propanesulfonic acid) buffer pH=7.
5. 50 μL water.

Two series of reaction mixtures were prepared, where one rare-earth metal was held constant (Gd or Lu) while the other was a variable rare-earth metal element (except Pm). To each well of the plate was added a glass ball of diameter 2 mm for mechanical stiffing. The well plate was sealed with transparent adhesive tape to prevent evaporation and was anchored to a shaker. The well-plate was shaken for 5 days at room temperature at 900 rpm. The well plate was then centrifuged and 50 μL of supernatant were taken from each well for determination of the metal concentration by ICP-OES (inductively coupled plasma atomic emission spectroscopy). The resulting absolute concentrations of both metals in the supernatant and their ratios are summarized in Table 1. Values of an M1/M2 ratio greater than or less than 1.0 indicate enrichment or depletion, respectively, of M1 relative to M2 in solution and thus demonstrate a degree of separation of the rare-earths.

TABLE 1

| | M2 = Gd | | | M2 = Lu | | |
|---|---|---|---|---|---|---|
| M1 | [mM] M1 | [mM] Gd | M1/Gd | [mM] M1 | [mM] Lu | M1/Lu |
| Sc | 5.882 | 0.295 | 19.94 | 5.49 | 4.903 | 1.12 |
| Y | 0.471 | 0.183 | 2.57 | 5.24 | 5.188 | 1.01 |
| La | 0.535 | 0.134 | 3.99 | 4.968 | 5.188 | 0.96 |
| Ce | 0.349 | 0.149 | 2.34 | 5.195 | 5.174 | 1.00 |
| Pr | 0.268 | 0.161 | 1.66 | 5.067 | 5.165 | 0.98 |
| Nd | 0.249 | 0.169 | 1.47 | 0.456 | 4.301 | 0.11 |
| Sm | 0.179 | 0.165 | 1.08 | 0.305 | 4.229 | 0.07 |
| Eu | 0.157 | 0.141 | 1.11 | 5.459 | 6.000 | 0.91 |
| Gd | 0.208 | 0.208 | 1.00 | 0.325 | 3.875 | 0.08 |
| Tb | 0.235 | 0.162 | 1.45 | 5.272 | 5.094 | 1.03 |
| Dy | 0.344 | 0.196 | 1.76 | 5.268 | 5.252 | 1.00 |
| Ho | 0.522 | 0.219 | 2.38 | 5.424 | 5.643 | 0.96 |
| Er | 5.697 | 5.127 | 1.11 | 5.558 | 5.298 | 1.05 |
| Tm | 2.653 | 0.239 | 11.10 | 5.453 | 5.423 | 1.01 |
| Yb | 4.218 | 0.279 | 15.12 | 5.226 | 5.148 | 1.02 |
| Lu | 4.93 | 0.291 | 16.94 | 5.403 | 5.403 | 1.00 |

Note:
partial evaporation of the solutions occurred during the course of the experiment, therefore some concentrations exceed the initial value of 5 mM, but the ratio of the two metals in a given well of the plate was unaffected.

Example 8) Separation of Binary Mixture of Rare-Earth Metals by Precipitation from Solution Using L1

Analogous to Example 7), two sets of reaction mixtures were prepared in a 96-well plate with the following differences: the stock solution of 3 M MOPS buffer had a pH of 8.5, the constant metals the series were either Er or Tm, each well-plate slot was equipped with one PTFE-coated magnetic stir bar, the well plate was sealed with a silicon cover, and the reaction mixtures were stirred on a magnetic stirrer for 2 days at room temperature. Analogous to Example 7), the well plate was then centrifuged and concentrations of the metals were determined using ICP-OES. The resulting concentrations of both metals in the supernatants and their ratios are summarized in Table 2. Values of an M1/M2 ratio greater than or less than 1.0 indicate enrichment or depletion, respectively, of M1 relative to M2 in solution and thus demonstrate a degree of separation of the rare-earths. It is evident from these results that a certain degree of separation is achieved even for a mixture of neighboring lanthanides (combinations Tm/Er and Er/Tm).

TABLE 2

| | M2 = Er | | | M2 = Tm | | |
|---|---|---|---|---|---|---|
| M1 | [mM] M1 | [mM] Er | M1/Er | [mM] M1 | [mM] Tm | M1/Tm |
| Sc | 5.191 | 4.469 | 1.16 | 5.087 | 4.448 | 1.14 |
| Y | 0.503 | 0.905 | 0.56 | 0.480 | 2.367 | 0.20 |
| La | 0.368 | 0.643 | 0.57 | 0.616 | 2.425 | 0.25 |
| Ce | 0.280 | 0.545 | 0.51 | 0.425 | 2.035 | 0.21 |
| Pr | 0.210 | 0.647 | 0.32 | 0.298 | 2.016 | 0.15 |
| Nd | 0.280 | 0.692 | 0.40 | 0.315 | 1.892 | 0.17 |
| Sm | 0.197 | 0.734 | 0.27 | 0.218 | 2.090 | 0.10 |
| Eu | 0.244 | 0.680 | 0.36 | 0.244 | 2.091 | 0.12 |
| Gd | 0.402 | 0.972 | 0.41 | 0.254 | 1.814 | 0.14 |
| Tb | 0.225 | 0.816 | 0.28 | 0.225 | 2.342 | 0.10 |
| Dy | 0.338 | 0.994 | 0.34 | 0.362 | 2.382 | 0.15 |
| Ho | 0.496 | 0.821 | 0.60 | 0.521 | 2.329 | 0.22 |
| Er | 4.969 | 4.969 | 1.00 | 2.759 | 3.368 | 0.82 |
| Tm | 3.971 | 2.292 | 1.73 | 4.779 | 4.779 | 1.00 |
| Yb | 5.400 | 4.304 | 1.25 | 5.477 | 4.598 | 1.19 |
| Lu | 7.607 | 4.564 | 1.67 | 7.337 | 4.588 | 1.60 |

Note:
partial evaporation of the solutions occurred during the course of the experiment, therefore some concentrations exceed the initial value of 5 mM, but the ratio of the two metals in a given well of the plate was unaffected.

Example 9) Separation of Binary Mixture of Rare-Earth Metals by Precipitation from Solution Using with L6

A series of reaction mixtures were prepared by pipetting into 2 mL plastic Eppendorf vials the following stock solutions:

1. 5 μL 100 mM aqueous solution of rare-earth element chloride number 1 (M1)
2. 5 μL 100 mM aqueous solution of $NdCl_3$.
3. 10 μL 100 mM aqueous solution of compound
4. 20 μL 3 M MOPS (3-(N-morpholino)propanesulfonic acid) buffer pH=7.
5. 50 μL water.

A PTFE-coated magnetic stir bar was added to each vial, and the vials were closed and stirred at 750 rpm at room temperature. After 18 hours, the stir bars were removed from the vials and the Eppendorf vials were centrifuged to separate the supernatant from the precipitate. 80 μL aliquots of the supernatants were removed from each vial and diluted by addition of 40 μL 1M HCl prior to analysis by ICP-OES for determination of the rare-earth content in each solution. The measured concentrations were adjusted to reflect the concentration of each rare-earth metal in the supernatant prior to dilution, and are reported in Table 3, as well as the M1/Nd ratios.

TABLE 3

| M1 | [mM] M1 | [mM] Nd | M1/Nd |
|---|---|---|---|
| Sc | 2.414 | 0.594 | 4.06 |
| Y | 1.592 | 1.463 | 1.09 |
| La | 0.620 | 0.606 | 1.02 |
| Ce | 0.596 | 0.556 | 1.07 |
| Pr | 0.524 | 0.559 | 0.94 |
| Nd | 0.496 | 0.496 | 1.00 |
| Sm | 0.541 | 0.512 | 1.06 |
| Eu | 0.711 | 0.566 | 1.26 |
| Gd | 0.195 | 0.166 | 1.18 |
| Tb | 0.428 | 0.178 | 2.40 |
| Dy | 0.459 | 0.135 | 3.41 |
| Ho | 1.943 | 0.618 | 3.14 |
| Er | 2.027 | 0.702 | 2.89 |
| Tm | 2.914 | 0.748 | 3.90 |
| Yb | 2.243 | 0.495 | 4.53 |
| Lu | 3.231 | 0.841 | 3.84 |

Example 10) Separation of Selected Industrially Relevant Binary Mixtures of Rare-Earth Metals by Precipitation from Solution Using L1, L2 and L3

Analogous to Example 7), three sets of reaction mixtures with two metals and either compound L1, L2, or L3 were prepared in a 96-well plate with the following differences: each well was equipped with one PTFE-coated magnetic stir bar, the well plate was sealed with a silicon cover, and the reaction mixtures were stirred on a magnetic stirrer for 2 days at room temperature. Analogous to Example 7), the well plate was then centrifuged and concentrations of the metals were determined using ICP-OES. The resulting absolute concentrations of both metals in the supernatants and their ratios are summarized in Table 4. Values of an M1/M2 ratio greater than or less than 1.0 indicate enrichment or depletion, respectively, of M1 relative to M2 in solution and thus demonstrate a degree of separation of the rare-earths. It is evident from the results that certain degrees of enrichment are achieved for very different combinations of metals, and that ligands L1, L2, and L3 have different selectivities for given combinations of metals.

TABLE 4

| | L1 | | | L2 | | | L3 | | |
|---|---|---|---|---|---|---|---|---|---|
| M1/M2 | [mM] M1 | [mM] M2 | M1/M2 | [mM] M1 | [mM] M2 | M1/M2 | [mM] M1 | [mM] M2 | M1/M2 |
| Nd/Ce | 0.397 | 0.038 | 10.45 | 0.425 | 0.779 | 0.55 | 0.000 | 0.745 | 0.00 |
| Pr/Ce | 0.186 | 0.285 | 0.65 | 0.162 | 0.171 | 0.95 | 0.060 | 0.021 | 2.86 |
| La/Ce | 0.603 | 0.388 | 1.55 | 0.175 | 0.158 | 1.11 | 0.111 | 0.036 | 3.08 |
| Nd/Dy | 0.204 | 0.302 | 0.68 | 1.757 | 1.970 | 0.89 | 0.000 | 0.025 | 0.00 |
| Tb/Dy | 0.216 | 0.284 | 0.76 | 1.054 | 2.708 | 0.39 | 0.010 | 0.027 | 0.37 |
| Pr/Dy | 0.216 | 0.157 | 1.38 | 2.417 | 2.422 | 1.00 | 0.018 | 0.034 | 0.53 |
| Tb/Eu | 0.206 | 0.159 | 1.30 | 1.182 | 0.956 | 1.24 | 0.018 | 0.017 | 1.06 |
| Nd/La | 0.177 | 0.559 | 0.32 | 0.263 | 0.128 | 2.05 | 0.000 | 0.102 | 0.00 |
| Pr/La | 0.246 | 0.569 | 0.43 | 0.172 | 0.163 | 1.06 | 0.014 | 0.098 | 0.14 |
| Nd/Pr | 0.530 | 0.572 | 0.93 | 2.303 | 2.352 | 0.98 | 0.000 | 0.016 | 0.00 |
| Tb/Pr | 0.116 | 0.211 | 0.55 | 1.945 | 2.156 | 0.90 | 0.015 | 0.018 | 0.83 |
| Nd/Tb | 0.325 | 0.142 | 2.29 | 1.532 | 1.438 | 1.07 | 0.008 | 0.008 | 1.00 |
| Tb/Y | 0.143 | 0.361 | 0.40 | 1.615 | 2.812 | 0.57 | 0.018 | 0.078 | 0.23 |
| Eu/Y | 0.118 | 0.265 | 0.45 | 1.363 | 2.814 | 0.48 | 0.016 | 0.076 | 0.21 |

Note:
A concentration of 0 mM indicate that the element was below the limit of detection.

Example 11) Separation of Ho/Er Mixture by Repeated Precipitation from Solution Using Compound L1

Stock solutions were pipetted into round-bottom 2 mL Eppendorf tubes as follows:

1. 10 μL 100 mM aqueous solution of $HoCl_3$
2. 10 μL 100 mM aqueous solution of $ErCl_3$
3. 20 μL 100 mM aqueous solution of compound L1.
4. 60 μL 2 M MOPS buffer pH=7.
5. 140 μL water.

Nine identical reaction mixtures were prepared and split into three groups: A, B, C. Each tube was equipped with one PTFE-coated magnetic stir bar and sealed, and the mixture was stirred on a magnetic stirrer for 24 hours at room temperature. The tubes were then centrifuged and the supernatants were carefully pipetted out and transferred to a new set of tubes. Precipitates from group A were dissolved by addition of 200 μL 0.1 M HCl. The concentrations of Ho and Er in the supernatants and in the re-dissolved precipitates from group A were determined by ICP-OES. Precipitates from groups B and C were further processed as follows: the precipitates were dissolved by addition of 100 μL 0.1 M HCl, and the pH of the solutions were then raised from 1 to 7 by addition of an equimolar amount of 0.2 M NaOH. The total volume was adjusted to 200 μL by addition of water. The prepared mixtures were subjected to a second round of precipitation and were stirred on a magnetic stirrer for 24 hours at room temperature. The tubes were again centrifuged and the supernatants were carefully pipetted out and transferred to a new set of tubes. Samples from group B were treated identically to the samples from group A previously, and the Ho and Er content in the supernatants and precipitates were determined by ICP-OES. Precipitates from group C were subjected to a third cycle of precipitation followed by Ho and Er content determination analogously to the procedures described above. The resulting absolute concentrations of both metals in the supernatants and precipitates, as well as calculated values of the separation factor Er/Ho according to the formula (concentration of Er in supernatant/concentration of Er in precipitate)/(concentration of Ho in supernatant/concentration of Ho in precipitate), are summarized in Table 5. The results demonstrate several important conclusions: 1—with the example of Ho and Er, it is proven that the separation method is usable even for neighboring lanthanides; 2—to achieve a higher degree of enrichment for one component, it is possible to repeat the precipitation; 3—triplicated samples prove good reproducibility of the process. The average of the separation factor values from all Er/Ho mixtures is 2.73 and is therefore comparable to or better than for extractants used for industrial liquid-liquid extraction, where the value of separation factor for two neighboring lanthanides is around 2.5 (Xie, F. et al. (2014), *Miner. Eng.* 56, 10-28).

TABLE 5

| | Supernatant concentration | | Precipitate concentration* | | Separation |
|---|---|---|---|---|---|
| Sample | [mM] Er | [mM] Ho | [mM] Er | [mM] Ho | factor Er/Ho |
| A1 | 0.86 | 0.44 | 4.03 | 4.72 | 2.30 |
| A2 | 0.90 | 0.40 | 3.69 | 4.31 | 2.59 |
| A3 | 0.99 | 0.46 | 3.61 | 4.29 | 2.55 |
| A average | 0.91 | 0.43 | 3.78 | 4.44 | |
| A std. deviation | 0.07 | 0.03 | 0.23 | 0.24 | |
| B1 | 1.16 | 0.58 | 2.62 | 4.07 | 3.10 |
| B2 | 0.99 | 0.51 | 3.08 | 4.24 | 2.68 |

TABLE 5-continued

| Sample | Supernatant concentration | | Precipitate concentration* | | Separation |
|---|---|---|---|---|---|
| | [mM] Er | [mM] Ho | [mM] Er | [mM] Ho | factor Er/Ho |
| B3 | 0.94 | 0.44 | 2.96 | 4.20 | 3.02 |
| B average | 1.03 | 0.51 | 2.88 | 4.17 | |
| B std. deviation | 0.12 | 0.07 | 0.24 | 0.09 | |
| C1 | 0.74 | 0.50 | 1.61 | 3.23 | 2.97 |
| C2 | 1.34 | 1.11 | 1.39 | 2.65 | 2.30 |
| C3 | 0.76 | 0.45 | 1.79 | 3.23 | 3.06 |
| C average | 0.95 | 0.69 | 1.60 | 3.04 | |
| C std. deviation | 0.34 | 0.37 | 0.20 | 0.33 | |

*Concentration of precipitate was determined after dissolution to a volume of 200 μL.

Example 12) Separation of Ho/Er Mixture by Precipitation Using Compound L1 and by Repeated Dissolution of the Precipitate with Heat The experiment was conducted according to Example 11), the difference being that instead of dissolving the precipitate in acid and neutralizing by addition of base, 200 μL of water were added to the precipitate and the suspension was stirred at 80° C. for 24 hours. Full dissolution of the precipitate was not achieved during this process, but a saturated solution was formed. After cooling to room temperature, the mixtures were processed as though the precipitation had occurred normally. The resulting absolute concentrations of both metals in the supernatants and precipitates, as well as calculated values of the separation factor Er/Ho according to the formula from Example 11) are summarized in Table 6. Data are directly comparable with those from Table 5 and prove that partial dissolution of the precipitate has a comparable effect to the repeated precipitation by method of complete dissolution of the precipitate in acid followed by neutralization. Repetition of the cycles in this experiment also led to a higher degree of enrichment for one of the rare-earth elements. The average separation factor value was 2.97.

TABLE 6

| Sample | Supernatant concentration | | Precipitate concentration* | | Separation |
|---|---|---|---|---|---|
| | [mM] Er | [mM] Ho | [mM] Er | [mM] Ho | factor Er/Ho |
| A1 | 0.85 | 0.36 | 3.70 | 4.53 | 2.89 |
| A2 | 0.86 | 0.36 | 3.75 | 4.46 | 2.84 |
| A3 | 0.80 | 0.33 | 3.73 | 4.68 | 3.04 |
| A average | 0.84 | 0.35 | 3.73 | 4.56 | |
| A std. deviation | 0.03 | 0.02 | 0.03 | 0.11 | |
| B1 | 0.52 | 0.27 | 2.78 | 3.89 | 2.69 |
| B2 | 0.69 | 0.32 | 2.92 | 3.98 | 2.94 |
| B3 | 0.70 | 0.25 | 2.76 | 3.64 | 3.69 |
| B average | 0.64 | 0.28 | 2.82 | 3.84 | |
| B std. deviation | 0.10 | 0.04 | 0.09 | 0.18 | |
| C1 | 0.62 | 0.39 | 2.11 | 3.16 | 2.38 |
| C2 | 0.64 | 0.37 | 1.94 | 3.13 | 2.79 |
| C3 | 0.63 | 0.27 | 2.52 | 3.75 | 3.47 |
| C average | 0.63 | 0.34 | 2.19 | 3.35 | |
| C std. deviation | 0.01 | 0.06 | 0.30 | 0.35 | |

*Concentration of precipitate was determined after dissolution to a volume of 200 μL.

Example 13) Separation of Gd/Lu Mixture by Repeated Precipitation from Solution Using Compound L1

Stock solutions were pipetted into round-bottom 2 mL Eppendorf tubes as follows:

1. 10 μL 100 mM aqueous solution of $GdCl_3$
2. 10 μL 100 mM aqueous solution of $LuCl_3$
3. 20 μL 100 mM aqueous solution of compound
4. 33.3 μL 3 M MOPS buffer pH=7.
5. 127.6 μL water.

Nine identical reaction mixtures were prepared and split into three groups A, B, C. Each tube was equipped with one PTFE-coated magnetic stir bar and sealed, and the mixture was stirred on a magnetic stirrer for 24 hours at room temperature. The tubes were then centrifuged and the supernatants were carefully pipetted out and transferred to a new set of tubes. Precipitates from group A were dissolved by addition of 100 μL 1 M HCl at room temperature over the course of 30 mins and then diluted to 200 μL by the addition of 100 μL water. Concentrations of Gd and Lu in the supernatants and in re-dissolved precipitates from group A were determined by ICP-OES. Precipitates from groups B and C were further processed as follows: the precipitates were dissolved by addition of 100 μL 1 M HCl at room temperature at pH 0 over the course of 30 mins, and the pH was then adjusted to approximately 7 by the addition of 50 μL 2 M NaOH, and the overall volume adjusted to 200 μL by the addition of water. The prepared mixtures were subjected to a second round of precipitation and were stirred on a magnetic stirrer for 24 hours at room temperature. Then, the tubes were again centrifuged and supernatants were carefully pipetted out and transferred to a new set of tubes. Samples from group B were treated identically to the samples from group A previously, and the Gd and Lu content in the supernatants and precipitates was determined by ICP-OES. Precipitates from group C were subjected to a third cycle of precipitation and followed by Gd and Lu content determination analogously to the procedures described above. The resulting absolute concentrations of both metals in the supernatants and precipitates, as well as the calculated values of the separation factor Lu/Gd according to the formula from Example 11), are summarized in Table 7. The average separation factor value was 43.7.

TABLE 7

| Sample | Supernatant concentration | | Precipitate concentration* | | Separation |
|---|---|---|---|---|---|
| | [mM] Gd | [mM] Lu | [mM] Gd | [mM] Lu | factor Lu/Gd |
| A1 | 0.54 | 4.35 | 4.38 | 1.08 | 33 |
| A2 | 0.21 | 4.12 | 4.22 | 0.98 | 84 |
| A3 | 0.40 | 4.36 | 4.12 | 0.90 | 50 |
| A average | 0.38 | 4.28 | 4.24 | 0.99 | |
| A std. deviation | 0.17 | 0.14 | 0.13 | 0.09 | |
| B1 | 0.21 | 0.80 | 3.33 | 0.23 | 55 |
| B2 | 0.61 | 0.83 | 3.40 | 0.21 | 22 |
| B3 | 0.20 | 0.77 | 3.70 | 0.22 | 65 |
| B average | 0.34 | 0.80 | 3.48 | 0.22 | |
| B std. deviation | 0.23 | 0.03 | 0.20 | 0.01 | |
| C1** | 2.33** | 0.24** | 1.33** | 0.05** | 3** |
| C2 | 0.56 | 0.17 | 2.86 | 0.07 | 12 |
| C3 | 0.23 | 0.16 | 2.45 | 0.06 | 28 |
| C average | 1.04 | 0.19 | 2.21 | 0.06 | |
| C std. deviation | 1.13 | 0.04 | 0.79 | 0.01 | |

*Concentration of precipitate was determined after dissolution to a volume of 200 μL.

**Sample C1 was an outlier and was discarded from calculation of average and standard deviation.

Example 14) Separation of Y/Tb Mixture by Repeated Precipitation from Solution Using Compound L2

The experiment was conducted according to Example 11) with 9 identical reaction mixtures containing Y, Tb, and compound L2. The experimental procedure was identical to that of Example 11). The resulting absolute concentrations of both metals in the supernatants and precipitates, as well as calculated values of separation factor Y/Tb according to the formula from Example 11), are summarized in Table 8. The average separation factor value was 3.34.

TABLE 8

| | Supernatant concentration | | Precipitate concentration* | | Separation factor |
|---|---|---|---|---|---|
| Sample | [mM] Y | [mM] Tb | [mM] Y | [mM] Tb | Y/Tb |
| A1 | 4.25 | 1.70 | 5.45 | 8.05 | 3.69 |
| A2 | 4.36 | 1.85 | 5.23 | 7.82 | 3.52 |
| A3 | 4.12 | 1.74 | 5.52 | 7.70 | 3.30 |
| A average | 4.24 | 1.76 | 5.40 | 7.86 | |
| A std. deviation | 0.12 | 0.08 | 0.15 | 0.18 | |
| B1 | 1.42 | 0.79 | 3.87 | 6.95 | 3.23 |
| B2 | 1.52 | 1.15 | 2.86 | 5.71 | 2.64 |
| B3 | 1.48 | 0.97 | 3.57 | 6.60 | |
| B average | 1.47 | 0.97 | 3.43 | 6.42 | |
| B std. deviation | 0.05 | 0.18 | 0.52 | 0.64 | |
| C1 | 1.91 | 1.25 | 1.67 | 5.24 | 4.79 |
| C2 | 1.20 | 1.03 | 2.43 | 5.70 | 2.73 |
| C3** | 0.36** | 1.92** | 0.00** | 1.18** | ** |
| C average | 1.56 | 1.14 | 2.05 | 5.47 | |
| C std. deviation | 0.50 | 0.16 | 0.54 | 0.33 | |

*Concentration of precipitate was determined after dissolution to a volume of 200 μL.
**Sample C3 was an outlier and was discarded from calculation of average and standard deviation.

Example 15) Separation of Eu/Yb Mixture by Precipitation from Solution Using Compound L5

Stock solutions were pipetted into round-bottom 2 mL Eppendorf tubes as follows:

1. 15 μL 100 mM aqueous solution of $EuCl_3$
2. 10 μL 100 mM aqueous solution of $YbCl_3$
3. 30 μL 100 mM aqueous solution of compound L5.
4. 90 μL 0.5 M MOPS buffer pH=7.

Three identical reaction mixtures were prepared. Each tube was equipped with one PTFE-coated magnetic stir bar and sealed, and the mixture was stirred on a magnetic stirrer for 24 hours at room temperature. The tubes were then centrifuged and the supernatants were carefully pipetted out and transferred to a new set of tubes. To the precipitate was added 100 μL 1 M HCl (reaching pH=0) and the mixture was stirred until full dissolution (overnight at room temperature, pH=0). The overall volume of the solution was adjusted to 150 μL volume by addition of water. The supernatants were treated with 1 M HCl for a total volume of 150 μL and pH=0.5. Concentrations of Eu and Yb in the supernatants and in the re-dissolved precipitates were determined by ICP-OES. The resulting absolute concentrations of both metals in the supernatants and precipitates, as well as calculated values of the separation factor Yb/Eu according to formula from Example 11), are summarized in Table 9. Triplicated samples prove good reproducibility of the process. The average separation factor value was 152.

TABLE 9

| | Supernatant concentration | | Precipitate concentration* | | Separation |
|---|---|---|---|---|---|
| Sample | [mM] Eu | [mM] Yb | [mM] Eu | [mM] Yb | factor Yb/Eu |
| 1 | 0.16 | 3.69 | 4.66 | 0.63 | 169 |
| 2 | 0.22 | 3.85 | 4.57 | 0.62 | 128 |
| 3 | 0.19 | 3.97 | 4.50 | 0.58 | 160 |
| Average | 0.19 | 3.84 | 4.58 | 0.61 | 152 |
| Std. deviation | 0.03 | 0.14 | 0.08 | 0.02 | 22 |

*Concentration of precipitate was determined after dissolution to a volume of 150 μL.

Example 16) Separation of Tb/Lu Mixture by Precipitation from Solution Using Compound L4

The experiment was conducted according to Example 24, with 3 identical reaction mixtures containing Tb, Lu, and compound L4. The experimental procedure was identical to that of Example 24 with the difference being that the dissolution of the precipitate in 100 μL, 1 M HCl was achieved within several minutes. The resulting absolute concentrations of both metals in the supernatants and precipitates, as well as calculated values of the separation factor Yb/Eu according to formula from Example 11), are summarized in Table 10. Triplicated samples prove good reproducibility of the process. The average separation factor value was 27.

TABLE 10

| | Supernatant concentration | | Precipitate concentration* | | Separation |
|---|---|---|---|---|---|
| Sample | [mM] Tb | [mM] Lu | [mM] Tb | [mM] Lu | factor Lu/Tb |
| 1 | 1.08 | 4.26 | 3.74 | 0.51 | 29 |
| 2 | 0.93 | 4.07 | 3.73 | 0.61 | 27 |
| 3 | 1.19 | 4.18 | 3.28 | 0.47 | 25 |
| Average | 1.07 | 4.17 | 3.59 | 0.53 | 27 |
| Std. deviation | 0.13 | 0.10 | 0.26 | 0.07 | 2 |

*Concentration of precipitate was determined after dissolution to a volume of 150 μL.

Example 17) Separation of Eu/Yb Mixture by Precipitation from Water/Acetonitrile Solutions Using Compound L5

3 reaction mixtures, differing in acetonitrile content (group A=10%, group B=20%, group C=50%) were prepared in plastic round-bottom 2 mL Eppendorf tubes, each in duplicate. For group A, the stock solutions were pipetted as follows: 5 μL 100 mM aqueous solution of $EuCl_3$; 5 μL 100 mM aqueous solution $YbCl_3$; 10 μL 100 mM aqueous solution of compound L5; 20 μL 3 M MOPS buffer pH=7; 50 μL water; 10 μL acetonitrile.

For group B, the stock solutions were pipetted as follows: 5 μL 100 mM aqueous solution of $EuCl_3$; 5 μL 100 mM aqueous solution $YbCl_3$; 10 μL 100 mM aqueous solution of compound L5; 20 μL 3 M MOPS buffer pH=7; 40 μL water; 20 μL acetonitrile. For group C, the stock solutions were pipetted as follows: 5 μL 100 mM aqueous solution of $EuCl_3$; 5 μL 100 mM aqueous solution $YbCl_3$; 10 μL 100 mM aqueous solution of compound L5; 20 μL 3 M MOPS buffer pH=7; 10 μL water; 50 μL acetonitrile.

Each tube was equipped with one PTFE-coated magnetic stir bar and sealed, and the mixture was stirred on a magnetic stirrer for 24 hours at room temperature. The tubes were then centrifuged and the supernatants were carefully pipetted out and transferred to a new set of tubes. To the precipitate was added 100 μL 1 M HCl and mixture was stirred until full dissolution (overnight at room temperature, pH=0). Concentrations of Eu and Yb in the supernatants and in the re-dissolved precipitates were determined by ICP-OES. The resulting absolute concentrations of both metals in the supernatants and precipitates, as well as calculated values of the separation factor Yb/Eu according to the formula from Example 11), are summarized in Table 11. The results demonstrate that separation by means of precipitation is achieved even in mixtures of water and a water-miscible organic solvent.

TABLE 11

| Sample | Supernatant concentration [mM] Eu | Supernatant concentration [mM] Yb | Precipitate concentration* [mM] Eu | Precipitate concentration* [mM] Yb | Separation factor Eu/Yb |
|---|---|---|---|---|---|
| A1 | 0.58 | 4.55 | 2.78 | 0.29 | 74 |
| A2 | 0.35 | 4.42 | 2.98 | 0.36 | 105 |
| A average | 0.47 | 4.48 | 2.88 | 0.32 | 90 |
| A std. deviation | 0.16 | 0.09 | 0.14 | 0.04 | 22 |
| B1 | 0.45 | 3.99 | 3.16 | 0.38 | 74 |
| B2 | 0.63 | 4.71 | 2.95 | 0.41 | 53 |
| B average | 0.54 | 4.35 | 3.06 | 0.40 | 64 |
| B std. deviation | 0.13 | 0.51 | 0.15 | 0.02 | 14 |
| C1** | 1.51** | 6.29** | 3.22 | 0.42 | 32 |
| C2** | 0.79** | 5.77** | 3.90 | 0.37 | 78 |
| C average | 1.15 | 6.03 | 3.56 | 0.39 | 55 |
| C std. deviation | 0.51 | 0.37 | 0.48 | 0.04 | 33 |

*Concentration of precipitate was determined after dissolution to a volume of 100 μL.

**Partial evaporation of the solution occurred in supernatants from Group C, therefore some concentrations exceeded values 5 mM, but the calculated separation factor was unaffected by it.

Example 18) Use of Additives to Improve Separations of Nd/Dy Mixture by Precipitation from Solution with Use of Compound L5

Stock solutions were pipetted into plastic 1×1 cm cuvettes to prepare reaction mixtures with concentrations as follows:

1. 11 mM chelator L5
2. 5 mM $NdCl_3$
3. 5 mM $DyCl_3$
4. 500 mM MOPS pH=7
5. the additive of interest, in a variable concentration; if possible, stock solutions were prepared from $Na^+$ salt forms of the compound; if not, the stock solutions were titrated by NaOH/HCl to pH=7 prior to addition (see Table 12 for additives and concentrations)

These aqueous reaction mixtures, each prepared to a total volume of 2.0 mL with the addition of water as necessary, were mixed by the use of a PTFE-coated stir bar on a magnetic stirrer. The cuvettes were sealed with transparent tape to prevent evaporation overnight. The reaction mixtures were stirred for 18 hours, at which point 500 μL aliquots of each reaction mixture were transferred into plastic 2 mL Eppendorf tubes and centrifuged. The supernatants were carefully pipetted out and transferred to a new set of tubes. The precipitate was dissolved by addition of 500 μL 1M HCl. The absolute concentration of Nd and Dy in each supernatant and precipitate was determined by ICP-OES. The resulting absolute concentrations of both metals in the supernatants and precipitates, as well as calculated values of the separation factor Dy/Nd according to the formula from Example 11), are summarized in Table 12. Where the supernatant Nd and Dy concentrations are recorded as 5 mM and the precipitate concentrations as 0 mM, no precipitation was observed, and therefore no separation was achieved by those conditions.

TABLE 12

| additive | Reaction [mM] Additive | Supernatant concentration [mM] Nd | Supernatant concentration [mM] Dy | Precipitate concentration* [mM] Nd | Precipitate concentration* [mM] Dy | Separation factor (Dy/Nd) |
|---|---|---|---|---|---|---|
| none | 0 | 0.07 | 0.37 | 4.98 | 4.60 | 5.5 |
| acetate | 50 | 0.33 | 3.05 | 4.97 | 2.43 | 19.0 |
| | 100 | 0.30 | 3.74 | 4.85 | 1.74 | 35.3 |
| | 250 | 1.17 | 4.37 | 4.04 | 1.05 | 14.4 |
| | 500 | 4.62 | 4.69 | 0.52 | 0.49 | 1.1 |
| benzoic acid | 20 | 0.13 | 1.09 | 4.94 | 3.83 | 10.8 |
| | 50 | 0.10 | 2.69 | 4.66 | 1.81 | 72.1 |
| | 100 | 0.49 | 4.03 | 4.60 | 0.97 | 38.9 |
| | 150 | 1.03 | 4.34 | 3.96 | 0.68 | 24.6 |
| | 200 | 2.89 | 4.20 | 1.65 | 0.53 | 4.6 |
| | 250 | 5 | 5 | 0 | 0 | N/A |
| chloride | 100 | 0.24 | 0.29 | 4.62 | 4.58 | 1.2 |
| | 200 | 0.12 | 0.22 | 4.57 | 4.48 | 1.8 |
| | 500 | 0.11 | 0.24 | 4.39 | 4.29 | 2.2 |
| | 1000 | 0.11 | 0.24 | 4.97 | 4.88 | 2.2 |
| citrate | 1 | 0.14 | 0.38 | 4.30 | 4.03 | 2.9 |
| | 5 | 0.19 | 1.24 | 4.77 | 3.62 | 8.6 |
| | 10 | 0.25 | 2.27 | 4.49 | 2.38 | 17.2 |
| | 20 | 0.66 | 3.52 | 4.08 | 1.21 | 18.1 |
| dipicolinic acid | 20 | 2.21 | 4.29 | 2.66 | 0.36 | 14.3 |
| fluoride | 5 | 0.13 | 1.21 | 6.21 | 4.87 | 11.6 |
| | 10 | 0.18 | 2.34 | 6.15 | 3.82 | 20.4 |
| | 15 | 0.49 | 3.26 | 5.68 | 2.72 | 13.9 |
| formate | 50 | 0.07 | 0.51 | 5.17 | 4.33 | 8.5 |
| | 100 | 0.42 | 1.09 | 4.85 | 3.84 | 3.2 |
| | 250 | 0.11 | 1.68 | 5.38 | 3.33 | 24.8 |
| | 500 | 0.22 | 2.51 | 4.93 | 2.09 | 27.2 |

TABLE 12-continued

| additive | Reaction [mM] Additive | Supernatant concentration [mM] Nd | Supernatant concentration [mM] Dy | Precipitate concentration* [mM] Nd | Precipitate concentration* [mM] Dy | Separation factor (Dy/Nd) |
|---|---|---|---|---|---|---|
| glycine | 50 | 0.09 | 1.01 | 4.90 | 3.60 | 15.1 |
| | 100 | 0.42 | 1.99 | 4.61 | 2.79 | 7.8 |
| | 150 | 0.11 | 2.25 | 4.91 | 2.44 | 42.0 |
| | 200 | 0.28 | 2.85 | 4.69 | 1.86 | 25.7 |
| glycolate | 5 | 0.09 | 1.73 | 4.64 | 2.61 | 33.3 |
| | 10 | 0.20 | 2.93 | 4.92 | 1.71 | 42.8 |
| | 15 | 0.35 | 3.13 | 4.54 | 1.11 | 37.1 |
| | 20 | 0.64 | 3.82 | 4.33 | 0.82 | 31.5 |
| α-HIBA (alpha-hydroxyisobutyric acid) | 5 | 0.10 | 1.55 | 4.32 | 2.59 | 26.5 |
| | 10 | 0.19 | 3.03 | 4.03 | 1.50 | 43.4 |
| | 15 | 0.33 | 3.37 | 4.33 | 1.18 | 37.2 |
| | 20 | 0.60 | 3.69 | 3.78 | 0.81 | 28.4 |
| l-lactate | 5 | 0.51 | 1.59 | 4.33 | 3.15 | 4.3 |
| | 10 | 0.21 | 2.47 | 4.49 | 2.08 | 25.8 |
| | 15 | 0.49 | 3.21 | 4.38 | 1.60 | 18.1 |
| | 20 | 0.50 | 3.57 | 4.33 | 1.18 | 26.3 |
| nitrate | 100 | 0.14 | 0.36 | 4.39 | 4.27 | 2.6 |
| | 200 | 0.15 | 0.41 | 3.97 | 3.89 | 2.9 |
| | 500 | 0.14 | 0.82 | 4.46 | 4.16 | 6.2 |
| | 1000 | 0.15 | 1.72 | 4.61 | 3.23 | 16.7 |
| phenylboronic acid | 20 | 0.08 | 0.31 | 5.02 | 4.33 | 4.3 |
| | 250 | 0.87 | 1.22 | 4.12 | 3.36 | 1.7 |
| picolinic acid | 20 | 5 | 5 | 0 | 0 | N/A |
| pyridine | 20 | 0.06 | 0.28 | 4.90 | 4.33 | 5.0 |
| | 250 | 0.09 | 0.41 | 4.67 | 4.02 | 5.3 |
| salicylic acid | 20 | 0.07 | 0.42 | 4.88 | 4.36 | 6.8 |
| s-mandelic acid | 20 | 0.47 | 3.77 | 4.52 | 1.13 | 32.4 |
| sulfate | 100 | 0.07 | 0.34 | 4.90 | 4.52 | 5.7 |
| | 250 | 0.08 | 0.47 | 4.96 | 4.09 | 7.4 |
| | 500 | 0.59 | 1.00 | 4.30 | 3.57 | 2.1 |
| | 1000 | 0.34 | 1.20 | 4.61 | 3.35 | 4.8 |
| thiocyanate | 100 | 0.14 | 0.31 | 4.66 | 4.46 | 2.3 |
| | 200 | 0.41 | 0.51 | 4.60 | 4.42 | 1.3 |
| | 500 | 0.36 | 0.72 | 4.65 | 4.16 | 2.2 |
| | 1000 | 0.41 | 1.70 | 4.63 | 3.26 | 5.8 |

*Concentration of precipitate was determined after dissolution to a volume of 500 μL.

Example 19) Separation of Nd/Pr Mixture by Repeated Precipitation from Solution Using Compound L5 and α-HIBA Stock solutions were pipetted into 4 mL glass vials to prepare reaction mixtures with concentrations as follows:

1. 11 mM (1.1 eq) chelator L5
2. 5 mM (0.5 eq) $PrCl_3$
3. 5 mM (0.5 eq) $NdCl_3$
4. 20 mM (4 eq) α-HIBA pH=6.5
5. 500 mM (50 eq) MOPS pH=7

Three aqueous reaction mixtures, numbered 1-3, were prepared with a total volume of 2 mL each and were treated identically throughout the process. A PTFE-coated magnetic stir bar was added to each and the reaction mixtures were stirred on a magnetic stirrer overnight at room temperature. After 18 hours, a 200 μL aliquot of the resulting suspension was taken from each vial and labelled as A1, A2, or A3, according to the reaction mixture number it was taken from. The aliquots were then centrifuged in a plastic Eppendorf centrifuge tube. The supernatant was carefully pipetted from each and transferred to a new set of tubes. To the precipitate was added 200 μL 1 M HCl and the mixture was stirred until full dissolution (about 1 hour at room temperature). The Nd and Pr content of these precipitate and supernatant samples was determined by ICP-OES. The remaining 1800 μL of reaction mixture were centrifuged in plastic Eppendorf centrifuge vials, and the supernatant was set aside. A sample of the supernatant was analysed on HPLC-MS and peak areas were compared to those of a standard 10 mM chelate solution; this allowed for calculation of the approximate concentration of chelate remaining in solution, and therefore of the quantity of chelate which had precipitated. The total volume for subsequent reactions was scaled according to this information, such that the concentration of chelate in solution prior to precipitation was 10 mM, even as the net quantity of chelate present was reduced. The precipitate, then, was dissolved by addition of 25 molar equivalents of 1 M HCl and transferred to a clean 4 mL glass vial with a PTFE-coated magnetic stir bar. 4 molar equivalents of α-HIBA were added to this vial, followed by 50 molar equivalents 3 M MOPS pH=7, the necessary calculated volume of water, and 25 molar equivalents 2 M NaOH to finish neutralising the reaction mixture. (The final reaction volume here was not so important as the final reaction concentrations.) The reaction mixtures were again stirred on a magnetic stirrer at room temperature overnight. After 18 hours, the resulting suspensions were treated in the same manner as before, with 200 μL aliquots (labelled as B1, B2, B3) taken for ICP-OES determination of the Nd and Pr content of the precipitate and supernatant. The remaining 1600 μL of reaction mixture were centrifuged, and the supernatant was analysed by HPLC-MS; the precipitate was treated as before to again yield a reaction solution with an initial concentration of 10 mM of chelate. The reaction mixtures were stirred overnight for the third repetition of processing, and 200 μL aliquots (C1, C2, C3) were again treated for ICP-OES determination of Nd and Pr content in the precipitate and supernatant after 18 hours. The resulting absolute concentrations of both metals in the supernatants and precipitates, as well as calculated values of the separation factor Nd/Pr according to the formula from Example 11), are summarized in Table 13. Triplicated samples prove good reproducibility of the process. The average separation factor was 1.69.

TABLE 13

| Sample | supernatant concentration [mM] Pr | [mM] Nd | precipitate concentration* [mM] Pr | [mM] Nd | separation factor Nd/Pr |
|---|---|---|---|---|---|
| A1 | 0.73 | 1.16 | 3.57 | 3.34 | 1.68 |
| A2 | 1.00 | 1.49 | 3.50 | 3.17 | 1.64 |
| A3 | 0.72 | 1.16 | 3.83 | 3.59 | 1.71 |
| A average | 0.82 | 1.27 | 3.63 | 3.37 | |
| A std dev | 0.16 | 0.19 | 0.17 | 0.21 | |
| B1 | 0.63 | 0.94 | 4.45 | 3.81 | 1.72 |
| B2 | 0.56 | 0.79 | 4.22 | 3.53 | 1.70 |
| B3 | 0.58 | 0.88 | 4.52 | 3.91 | 1.76 |
| B average | 0.59 | 0.87 | 4.40 | 3.75 | |
| B std dev | 0.04 | 0.07 | 0.15 | 0.19 | |
| C1 | 0.66 | 0.87 | 4.70 | 3.70 | 1.69 |
| C2 | 0.74 | 0.93 | 4.31 | 3.29 | 1.66 |
| C3 | 0.56 | 0.75 | 4.98 | 4.06 | 1.66 |
| C avg | 0.65 | 0.85 | 4.66 | 3.68 | |
| C std dev | 0.09 | 0.09 | 0.33 | 0.39 | |

*Concentration in the precipitate was determined after dissolution for a total volume of 200 μL.

Example 20) Separation of Tb/Dy Mixture by Repeated Precipitation from Solution Using Compound L5 and α-HIBA Analogous to Example 19, three reaction mixtures were prepared with the following changes: the rare-earth elements were Tb and Dy, and 0.5 molar equivalents (5 mM reaction concentration) of α-HIBA were used. Otherwise, the experiment was run analogously to Example 19.

The resulting absolute concentrations of both metals in the supernatants and precipitates, as well as calculated values of the separation factor Dy/Tb according to the formula from Example 11), are summarized in Table 14. Triplicated samples prove good reproducibility of the process. The average separation factor was 2.32.

TABLE 14

| Sample | supernatant concentration [mM] Tb | [mM] Dy | precipitate concentration* [mm] Tb | [mM] Dy | separation factor Dy/Tb |
|---|---|---|---|---|---|
| A1 | 0.77 | 1.41 | 3.85 | 3.02 | 2.34 |
| A2 | 0.82 | 1.47 | 3.75 | 2.88 | 2.33 |
| A3 | 0.86 | 1.59 | 3.62 | 2.92 | 2.30 |
| A average | 0.82 | 1.49 | 3.74 | 2.94 | |
| A std dev | 0.05 | 0.09 | 0.12 | 0.07 | |
| B1 | 0.84 | 1.27 | 4.08 | 2.65 | 2.33 |
| B2 | 0.90 | 1.30 | 4.30 | 2.72 | 2.28 |
| B3 | 0.79 | 1.26 | 4.11 | 2.76 | 2.38 |
| B average | 0.84 | 1.27 | 4.16 | 2.71 | |
| B std dev | 0.06 | 0.02 | 0.12 | 0.06 | |
| C1 | 0.90 | 1.10 | 4.66 | 2.52 | 2.26 |
| C2 | 0.98 | 1.20 | 4.62 | 2.42 | 2.34 |
| C3 | 0.83 | 1.08 | 4.83 | 2.72 | 2.33 |
| C avg | 0.90 | 1.13 | 4.70 | 2.55 | |
| C std dev | 0.08 | 0.06 | 0.11 | 0.15 | |

TABLE 14-continued

*Concentration in the precipitate was determined after dissolution for a total volume of 200 μL.

Example 21) Separation of Nd/Pr/Tb/Dy Mixture by Precipitation from Solution Using Compound L5

Stock solutions were pipetted into 4 mL glass vials to prepare reaction mixtures with concentrations as follows:

1. 38.5 mM (1.1 eq) chelator L5
2. 35 mM (1 eq) total $LnCl_3$ content (from a stock solution containing a mixture of Ln=Nd, Pr, Tb, and Dy, in a ratio of 3.3:1:1:1, Nd:Pr:Tb:Dy)
3. 1750 mM (50 eq) MOPS pH=7

The total reaction volume was 3.2 mL. A PTFE-coated stir bar was added to this vial, and the vial was capped and stirred with the temperature maintained at 40° C. by use of an aluminium heating block on a magnetic stirrer. After 20 hours, a 500 μL aliquot of the reaction mixture was taken from the vial. This was centrifuged in a 2 mL plastic Eppendorf centrifuge vial, and the supernatant was carefully pipetted from this and transferred to a new set of tubes. The precipitate was dissolved by addition of 500 μL 1 M HCl, and the absolute concentration of Nd, Pr, Tb, and Dy in both the supernatants and precipitates was determined by ICP-OES.

The resulting absolute concentrations of the four metals in the supernatants and precipitates are summarized in Table 15. The percent molar composition of each phase is also provided, showing the minimal selectivity in precipitation under these conditions.

TABLE 15

| Ln | Composition of Ln stock solution | solution after 20 hrs mM | composition | precipitate* after 20 hrs mM | composition |
|---|---|---|---|---|---|
| Nd | 52% | 1.85 | 54.3% | 16.68 | 53.0% |
| Pr | 16% | 0.47 | 13.9% | 4.85 | 15.4% |
| Tb | 16% | 0.50 | 14.7% | 5.28 | 16.8% |
| Dy | 16% | 0.58 | 17.1% | 4.69 | 14.9% |

*Concentration in the precipitate was determined after dissolution for a total volume of 500 μL.

Example 22) Separation of Nd/Pr/Tb/Dy Mixture by Precipitation from Solution Using Compound L5 and Acetate A reaction mixture was prepared analogously to Example 21), with the differences being the use of sodium acetate buffer pH=5.8 in place of MOPS pH=7, an additional aliquot taken for analysis after 2 days, and the lack of ICP-OES analysis on the precipitated portions of the solution—that is, only the supernatants were analysed. Otherwise, the reaction was run analogously to Example 21). The resulting absolute concentrations of the four metals in the supernatants are summarized in Table 16. The percent molar composition of each is also provided, showing the improved selectivity in precipitation under these conditions, compared to Example 21).

TABLE 16

| | Composition of Ln | solution after 20 hrs | | solution after 2 days | |
|---|---|---|---|---|---|
| Ln | stock solution | mM | composition | mM | composition |
| Nd | 52% | 17.01 | 51.5% | 6.42 | 36.1% |
| Pr | 16% | 4.78 | 14.5% | 1.57 | 8.8% |
| Tb | 16% | 5.84 | 17.7% | 4.77 | 26.9% |
| Dy | 16% | 5.41 | 16.4% | 5.00 | 28.1% |

Example 23) Separation of Nd/Pr/Tb/Dy Mixture by Precipitation from Solution Using Compound L5 and α-HIBA Stock solutions were pipetted into plastic 1×1 cm cuvettes to prepare reaction mixtures with concentrations as follows:

1. 16.7 mM (1.1 eq) chelator L5
2. 15 mM (1 eq) total $LnCl_3$ content (from a stock solution containing a mixture of Ln=Nd, Pr, Tb, and Dy, in a ratio of 3.3:1:1:1, Nd:Pr:Tb:Dy)
3. 15 mM (1 eq) α-HIBA (alpha-hydroxyisobutyric acid)
4. 760 mM (50 eq) MOPS pH=7

These aqueous reaction mixtures, each prepared to a total volume of 1.5 mL with the addition of water as necessary, were mixed by the use of a PTFE-coated stir bar on a magnetic stirrer. The cuvettes were sealed with transparent tape to prevent evaporation overnight. The reaction mixtures were stirred for 18 hours, at which point 500 μL aliquots of each reaction mixture were transferred into plastic 2 mL Eppendorf tubes and centrifuged. The supernatants were carefully pipetted out and transferred to a new set of tubes. The precipitate was dissolved by addition of 500 μL 1M HCl. The absolute concentration of the four metals in each supernatant and precipitate was determined by ICP-OES. The resulting absolute concentrations of the four metals in the supernatants and precipitates are summarized in Table 17, as well as the percent composition of each phase, demonstrating the improved selectivity by this method against Example 21). Triplicated samples prove good reproducibility.

TABLE 17

| | supernatant concentration | | | | precipitate concentration* | | | |
|---|---|---|---|---|---|---|---|---|
| sample | Nd | Pr | Tb | Dy | Nd | Pr | Tb | Dy |
| A | 1.31 | 0.32 | 1.22 | 1.73 | 8.60 | 2.30 | 1.25 | 1.04 |
| B | 0.78 | 0.20 | 1.00 | 1.38 | 7.83 | 2.08 | 1.11 | 0.95 |
| C | 0.98 | 0.24 | 1.17 | 1.65 | 8.96 | 2.40 | 1.25 | 1.05 |
| average | 1.03 | 0.25 | 1.13 | 1.59 | 8.46 | 2.26 | 1.20 | 1.01 |
| std dev | 0.27 | 0.06 | 0.11 | 0.18 | 0.58 | 0.16 | 0.08 | 0.05 |
| % comp | 25.7% | 6.3% | 28.3% | 39.7% | 65.4% | 17.5% | 9.3% | 7.8% |

*Concentration in the precipitate was determined after dissolution to a volume of 500 μL.

Example 24) Separation of Nd/Pr/Tb/Dy Mixture by Repeated Precipitation from Solution Using Compound L5 and α-HIBA The reaction mixture was prepared by pipetting the following aqueous stock solutions into a 20 mL glass vial:

1. 476 μL 246 mM aqueous chelator L5
2. 606 μL 175.5 mM aqueous $LnCl_3$ solution (from a stock solution containing a mixture of Ln=Nd, Pr, Tb, and Dy, in a ratio of 3.3:1:1:1, Nd:Pr:Tb:Dy)
3. 41.6 μL 2560 mM aqueous α-HIBA pH=6.5
4. 4103 μL water
5. 1733 μL 3.0 M MOPS pH=7

The total reaction volume was 7.0 mL. Three identical reaction mixtures were prepared. A PTFE-coated stir bar was added to each vial; the vials were capped and stirred on a magnetic stirrer at room temperature. After 18 hours, a 200 μL aliquot of the reaction mixture was taken from each vial. This was centrifuged in a 2 mL plastic Eppendorf centrifuge tube, and the supernatant was carefully pipetted from the sample and transferred to a new set of tubes. The precipitate was dissolved by addition of 200 μL 1 M HCl, and the absolute concentration of each of the four lanthanides (Nd, Pr, Tb, and Dy) in each sample of the supernatant and precipitate was determined by ICP-OES. The remaining reaction mixtures from each vial were individually centrifuged in 15 mL plastic centrifuge tubes to separate the precipitate from the supernatant. The supernatant was discarded. Each precipitate was dissolved by addition of 2 mL 1 M HCl and heating to 80° C. for 1 hour. After dissolution, the acidic solutions were transferred to clean 20 mL glass vials with one PTFE-coated magnetic stir bar each. To each solution was added, in order: 2037 μL water, 40.4 μL 2560 mM aqueous α-HIBA pH=6.5, 1723 μL 3 M aqueous MOPS pH=7, and 1000 μL 2 M NaOH. These solutions were capped and stirred on a magnetic stirrer at room temperature. After 18 hours, a 200 μL aliquot of the reaction mixture was again taken from each and treated for ICP-OES analysis as before. Once again, the remaining reaction mixtures from each vial were individually centrifuged in 15 mL plastic centrifuge tubes to separate the precipitate from the supernatant. The supernatant was discarded. Each precipitate was dissolved by addition of 1 mL 1M HCl and heating to 80° C. for 1 hour. After dissolution, the acidic solutions were transferred to clean 20 mL glass vials with one PTFE-coated magnetic stir bar each. To each solution was added, in order: 3376 μL water, 51.6 μL 2560 mM aqueous α-HIBA pH=6.5, 1672 μL 3 M aqueous MOPS pH=7, and 500 μL 2 M NaOH. These solutions were capped and stirred on a magnetic stirrer at room temperature. After 18 hours, a final 200 μL aliquot of the reaction mixture was again taken from each vial and treated for ICP-OES analysis as before. The resulting absolute concentrations of the four metals in the supernatants are summarized in Table 18. Triplicated samples prove good reproducibility of the process.

TABLE 18

| | supernatant concentration [mM] | | | | precipitate concentration [mM] | | | |
|---|---|---|---|---|---|---|---|---|
| sample | Nd | Pr | Tb | Dy | Nd | Pr | Tb | Dy |
| A1 | 0.85 | 0.12 | 1.23 | 1.69 | 8.82 | 2.39 | 1.05 | 0.81 |
| A2 | 0.90 | 0.15 | 1.19 | 1.65 | 8.69 | 2.35 | 1.07 | 0.82 |
| A3 | 0.70 | 0.09 | 1.20 | 1.68 | 8.55 | 2.32 | 1.06 | 0.82 |
| A avg | 0.82 | 0.12 | 1.21 | 1.67 | 8.68 | 2.35 | 1.06 | 0.81 |
| A std dev | 0.10 | 0.03 | 0.02 | 0.02 | 0.14 | 0.03 | 0.01 | 0.01 |
| A avg composition | 21.4% | 3.2% | 31.6% | 43.8% | 67.2% | 18.2% | 8.2% | 6.3% |
| B1 | 0.65 | 0.06 | 0.60 | 0.50 | 7.54 | 2.11 | 0.41 | 0.20 |
| B2 | 0.60 | 0.05 | 0.61 | 0.52 | 7.82 | 2.20 | 0.42 | 0.21 |
| B3 | 0.59 | 0.05 | 0.64 | 0.54 | 8.02 | 2.24 | 0.45 | 0.22 |
| B avg | 0.61 | 0.06 | 0.62 | 0.52 | 7.80 | 2.18 | 0.42 | 0.21 |
| B std dev | 0.03 | 0.01 | 0.02 | 0.02 | 0.24 | 0.07 | 0.02 | 0.01 |
| B avg composition | 34.0% | 3.1% | 34.1% | 28.7% | 73.4% | 20.6% | 4.0% | 2.0% |
| C1 | 0.67 | 0.07 | 0.24 | 0.12 | 6.34 | 1.85 | 0.15 | 0.03 |
| C2 | 0.68 | 0.07 | 0.25 | 0.12 | 6.40 | 1.87 | 0.15 | 0.04 |
| C3 | 0.83 | 0.10 | 0.27 | 0.13 | 6.17 | 1.80 | 0.16 | 0.04 |
| C avg | 0.73 | 0.08 | 0.26 | 0.12 | 6.30 | 1.84 | 0.15 | 0.04 |
| C std dev | 0.09 | 0.02 | 0.01 | 0.01 | 0.12 | 0.03 | 0.01 | 0.00 |
| C avg composition | 61.4% | 6.5% | 21.6% | 10.4% | 75.6% | 22.1% | 1.8% | 0.5% |

III. Isolation of Components after Separations by Precipitation

Example 25) Removal of Additive from Remaining Solution after Precipitation by Ultrafiltration Stock solutions were pipetted into 20 mL glass vials to prepare reaction mixtures with concentrations as follows:

1. 16.7 mM chelator L5
2. 15.2 mM total $LnCl_3$ content (from a stock solution containing a mixture of Ln=Nd, Pr, Tb, and Dy, in a ratio of 3.3:1:1:1, Nd:Pr:Tb:Dy)
3. a variable concentration of the additive The reaction solution was then titrated to pH 6.5 by addition of aqueous NaOH (2 M). The solution was stirred on a magnetic stir-plate at room temperature for 2 hours, at which point the precipitate was separated from the solution by filtration through a 0.45 μm regenerated cellulose syringe filter. A sample of this solution was taken for HPLC analysis. The solution was then filtered on an ultrafiltration system with a nanofiltration membrane with molecular weight cut-off of 100-250 Da (NFS membrane, Synder Filtration, CA, USA), 4 bar $N_2$ to pressurize the system, magnetic stirring, and continual addition of water to replace the filtered volume. The filtrate was collected in 1.5 mL fractions; the chelate and additive present in these fractions were quantified by HPLC-DAD and compared to the measured values for the sample taken from the solution prior to ultrafiltration. The concentration of each component (chelate and additive) which passed through the ultrafiltration membrane was considered as a percentage, calculated as the ratio of the peak area in the filtrate sample to the peak area for the initial solution (after accounting for the difference in dilution factors when preparing the samples for HPLC analysis). Table 19 summarizes these results for each additive used. For samples with benzoic acid as the additive, the HPLC method was a gradient from 5% to 100% $MeCN/H_2O$ (aqueous phase 0.01% HCOOH; 1-minute equilibration period, a 4-minute gradient to 100% MeCN, a 1-minute wash, a 0.5-minute gradient to 5% MeCN, and a 3.5-minute re-equilibration period) on a Luna Omega Polar C18 column (150×4.6 mm, 5 μm); flow rate 1.0 mL/min; detection by diode-array detector. For samples with alpha-hydroxyisobutyric acid or acetic acid as the additive, the HPLC method was a gradient from 5% to 50% $MeCN/H_2O$ (aqueous phase 0.01M phosphoric acid buffer, pH=2.5; 1-minute equilibration period, a 2-minute gradient to 50% MeCN, a 0.5-minute gradient to 5% MeCN, and a 1.5-minute re-equilibration period); Phenomenex Kinetex C18 column (100×3 mm, 2.6 μm); flow rate 0.6 mL/min; detection by diode-array detector. Peak areas for alpha-hydroxyisobutyric acid and acetic acid were integrated at 210 nm, and for the lanthanide chelates and benzoic acid, at 280 nm

TABLE 19

| additive | initial [additive] (mM) | % of initial [chelate] in filtrate | % of initial [additive] in filtrate |
|---|---|---|---|
| α-HIBA | 30.4 | 0.4% | 3% |
| benzoic acid | 76 | 0.3% | 43% |
| acetate | 76 | 0.8% | 83% |

Example 26) Use of Ultrafiltration to Remove Benzoic Acid from Solution and Effect Precipitation of L5 Complexes from Solution Stock solutions were pipetted into a 20 mL glass vial to prepare the reaction mixture:

1. 938 μL 196 mM aqueous chelator L5 (pH=4)
2. 836 μL 1000 mM aqueous benzoic acid (stock solution containing 1 equivalent NaOH)
3. 8000 μL $H_2O$
4. 952 μL 175.5 mM aqueous $LnCl_3$ solution (from a stock solution containing a mixture of Ln=Nd, Pr, Tb, and Dy, in a ratio of 3.3:1:1:1, Nd:Pr:Tb:Dy)

The reaction solution was then titrated to pH 6.5 by addition of aqueous 2 M NaOH. The solution was stirred on a magnetic stir-plate at room temperature for 1 hour, and the precipitate was removed from the solution by filtration through a 0.45 μm regenerated cellulose syringe filter. From this filtered solution, 1 mL was set aside for elemental analysis as the "initial" solution, 1 mL was set aside as a "control" solution in a clean 4 mL glass vial with a PTFE-coated stir bar to be stirred at 600 rpm at room temperature on a magnetic stirrer, and the remaining 9 mL were diluted slightly by addition of 2 mL $H_2O$, then filtered on an ultrafiltration system with a nanofiltration membrane with molecular weight cut-off of 100-250 Da (NFS membrane, Synder Filtration, CA, USA), 4 bar $N_2$ to pressurize the system, magnetic stiffing at 250 rpm, and continual addition of water to replace the filtered volume. The filtrate was collected in an Erlenmeyer flask, and a total volume of 50 mL was filtered over 11 hours. After this time, the "retained" reaction mixture, now having a volume of 10.5 mL and with some precipitate present, was transferred to a clean 20 mL glass vial and stirred by PTFE-coated stir bar on a magnetic stirrer at 600 rpm for an additional 10 hours, as was the control solution. After this additional time, samples of both the control solution and the retained solution from the ultrafiltration were prepared for elemental analysis by filtration through 0.45 μm nylon syringe filters. The initial, control, and retained solutions were then analysed by ICP-OES for determination of absolute Nd, Pr, Dy, and Tb content.

The absolute Ln content of the samples is shown in Table 20. The measured contents of the control sample do not differ significantly from the initial solution, proving that no precipitation occurred during the additional reaction time for the control sample. The contents of the retained sample, however, are significantly lower than the initial and control samples, and the difference is greater than that which could be accounted for by the changes in volume which occurred during the ultrafiltration process. These results therefore prove that by the use of ultrafiltration to remove the additive from the reaction solution, the soluble complexes can be caused to precipitate without the use of energy-intensive evaporation methods.

TABLE 20

| | concentration [mM] | | | | |
|---|---|---|---|---|---|
| sample | Pr | Nd | Tb | Dy | sum of M |
| initial | 0.40 | 1.80 | 0.76 | 0.77 | 3.73 |
| control | 0.40 | 1.80 | 0.75 | 0.76 | 3.71 |
| retained | 0.23 | 1.03 | 0.42 | 0.44 | 2.12 |
| retained* | 0.27 | 1.20 | 0.49 | 0.51 | 2.47 |

*Concentration recalculated from the end volume of 10.5 to the original volume of 9.0 mL.

Example 27) Dissociation of [La(L5)] Complex in Acidic Environment and Separation of Free Compound L5 from Free Ion $La^{3+}$ A solution with the complex of compound L5 and $La^{3+}$ ions was prepared in a 2 mL round-bottom Eppendorf tube by mixing of the following solutions:

1. 10 μL 100 mM aqueous solution of $LaCl_3$.
2. 10 μL 100 mM aqueous solution of compound L5.
3. 100 μL 0.5 M MOPS buffer pH=7.
4. 880 μL water.

The reaction mixture was thoroughly mixed and left for 10 minutes at room temperature. Two 200 μL samples were then taken. One was analysed directly by HPLC-MS (high-performance liquid chromatography-mass spectrometry). The second was acidified by 1 μL of TFA, mixed thoroughly, and allowed to equilibrate for 30 minutes at room temperature (pH of the mixture was 3). The acidified sample was then analysed on HPLC-MS. A third sample was prepared as a solution of 1 mM compound L5 in 50 mM MOPS pH=7 buffer as a reference and was also analysed by HPLC-MS. The method of analysis was the same for all three samples (injection volume 1 μL, Phenomenex Kinetex C18 column, 100×3 mm, 2.6 μm; isocratic method with 23.5% acetonitrile, 76.5% aqueous solution of 10 mM ammonium formate pH=7.0, flow rate 0.65 mL/min; detection by diode-array detector at 280 nm and by mass spectrometer). The chromatograms for all three samples at 280 nm are depicted in FIG. 1, which shows a clear difference in retention time of the intact complex [La(L5)] and free compound L5. The sample of [La(L5)] which was acidified by TFA shows partial dissociation to compound L5 and free $La^{3+}$ ions; the latter cannot be directly detected by this method. The MS spectra confirm these results: the peak at 6.4 minutes is [La(L5)] complex (m/z for ion $[(M+H)^+]$: calculated 623.1; found 623.2), while the peak at 3.1 minutes is free compound L5 (m/z for ion $[(M+H)^+]$: calculated 487.3; found 487.3). The retention time of the free compound L5 (3.1 minutes) is sufficient for this compound to be separated from free $La^{3+}$ ions, which are not retained on a C18 reverse-phase column and elute within the dead volume of the system (2.7 minutes). Reducing the organic solvent used in the isocratic method would also increase the differences in the retention times of the species.

Example 28) Separation of Pr from L5 by the Use of C18 Column Separations

Stock solutions were pipetted into a 20 mL glass vial to prepare a reaction mixture as follows:

1. 1.00 mL 100 mM aqueous solution of $PrCl_3$
2. 0.60 mL 218 mM aqueous solution of L5

NaOH (2 M aqueous stock solution) was added by micropipette to titrate the reaction pH to 6. This reaction was stirred by the use of a PTFE-coated stir bar on a magnetic stirrer at room temperature for 30 minutes. The resulting suspension was transferred into two 2 mL plastic Eppendorf centrifuge tubes and centrifuged. The supernatant was set aside and analysed by HPLC, and the precipitate was dissolved by addition of 0.15 mL 1 M HCl to each Eppendorf tube. These dissolved solutions were combined and titrated to pH 2 by addition of 2 M NaOH.

The L5 and Pr present in the acidic solution were separated by reverse-phase chromatography, using 1.01 g fully-endcapped C18 silica gel in a plastic SPE cartridge (2 cm diameter). After conditioning the reversed phase with MeCN and MeCN/$H_2O$ solutions, 1 mL of $H_2O$ was run through the column before loading the L5-Pr solution onto the column. MeCN/$H_2O$ solutions were used to elute the components from the column: 2 mL 0% MeCN, 4 mL 10% MeCN, 4 mL 25% MeCN, and 4 mL 50% MeCN. The eluted solutions were collected as seven 2 mL fractions. All fractions were analysed by HPLC-MS to determine L5 content. The first two fractions were also analysed by ICP-OES to determine Pr content. Later fractions, which were shown by HPLC-MS to contain L5, were not analysed for Pr content by ICP-OES, because HPLC-MS samples of those fractions with the addition of a pH=7 MOPS buffer showed no evidence of L5-Pr complex formation, which would have been observed if Pr was present in those fractions with L5.

The distribution of L5 and Pr in the fractions is shown in Table 21, where the quantity of each component present in each fraction is provided as a fraction of the total quantity of the component found in the sum of the fractions, as well as the measured content of Pr (in mM) and L5 (as the integrations of the chromatographic peak areas at 280 nm) found in each fraction. These results demonstrate that the chelator and the free rare earth metal ions can be separated from each other after treatment, allowing the chelator to be recycled and reused, and the rare earth elements to be isolated in the form of aqueous solutions of soluble salts.

TABLE 21

| Fraction | measured content of fraction | | % distribution in fractions | |
|---|---|---|---|---|
| | Pr | L5 peak area | Pr | L5 |
| (% MeCN) | (mM) | (280 nm, AU) | | |
| 1 (0%) | 18.95 | 0 | 87% | 0.0% |
| 2 (10%) | 2.82 | 3 | 13% | 0.1% |
| 3 (10%) | — | 2258 | — | 56.8% |
| 4 (25%) | — | 1382 | — | 34.8% |
| 5 (25%) | — | 324 | — | 8.1% |
| 6 (50%) | — | 5 | — | 0.1% |
| 7 (50%) | — | 3 | — | 0.1% |

IV. Isolation of Rare-Earth Elements from NdFeB Magnets

Example 29) Separation of Rare-Earths from Transition Metals by Use of Ammonium Oxalate A spherical nickel-coated NdFeB magnet (105 mg) was placed in a 4 mL glass vial and dissolved by addition of 1.00 mL concentrated (~65%) nitric acid. The resulting solution was analysed by ICP-OES to quantify the major components present (Table 22; step 1). To isolate the lanthanides Nd and Pr from this solution, the solution was treated with ammonium oxalate: 0.1 mL of the nitric acid solution (approximately 1.6 M total dissolved metal content) was added to an aqueous solution of ammonium oxalate (1.1 mL, 0.5 M; ~3.5 molar equivalents of ammonium oxalate to metal) in a 2 mL plastic Eppendorf vial. The solution was mixed thoroughly and this immediately yielded a bright green solution and a white precipitate, which were separated by centrifugation. The solution was analysed by ICP-OES to quantify the metals present (Table 22; step 2); Nd and Pr were not detected in this solution, but had precipitated as insoluble lanthanide oxalates. This precipitate was rinsed with water, then dissolved by the addition of 100 µL concentrated nitric acid to the plastic Eppendorf vial. After five minutes, NaOH (1.0 mL, 2 M) was added to the solution to yield the lanthanide hydroxides as a white precipitate. The precipitate was again isolated by centrifugation and rinsed with water before dissolution in HCl (200 µL, 0.5 M). This solution of lanthanide chlorides was analysed by ICP-OES to determine its final composition (Table 22; step 3).

Table 22 shows the concentration of each component of the resulting solutions after each step of the process, as well as the percent molar compositions. This method allows for isolation of a pure (99%) mixture of lanthanides from an NdFeB magnet which is composed of less than 10% lanthanides by molar composition.

TABLE 22

| element | step 1 | | step 2 | | step 3 | |
|---|---|---|---|---|---|---|
| | mM | molar % | mM | molar % | mM | molar % |
| Fe | 1311.76 | 83.4% | 80.38 | 90.0% | 0.25 | 0.5% |
| Ni | 27.22 | 1.7% | 1.73 | 1.9% | 0.06 | 0.1% |
| B | 98.43 | 6.3% | 6.18 | 6.9% | 0.00 | 0.0% |
| Nd | 96.64 | 6.1% | 0.00 | 0.0% | 39.36 | 77.2% |
| Pr | 24.42 | 1.6% | 0.00 | 0.0% | 11.20 | 22.0% |
| Cu | 14.65 | 0.9% | 1.02 | 1.1% | 0.09 | 0.2% |

The invention claimed is:

1. A method for separation of rare-earth elements by precipitation, comprising the following steps:

a) Providing an aqueous solution of ions of at least two different rare-earth elements ($M^{3+}$) to be separated, and an aqueous solution of a compound of general formula (I)

(I)

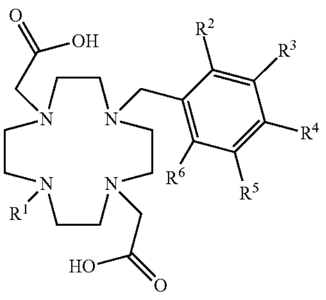

wherein $R^1$ is selected from the group consisting of H and —$CH_2COOH$;

$R^2$, $R^3$, $R^4$, $R^5$ and $R^6$ are independently selected from the group consisting of —H, OH, —$NO_2$, —COOH, and phenyl;

and/or $R^2$ and $R^3$ together with two neighbouring carbon atoms of the aromatic ring form a six-membered aromatic ring;

and/or $R^3$ and $R^4$ together with two neighbouring carbon atoms of the aromatic ring form a six-membered aromatic ring;

and/or $R^4$ and $R^5$ together with two neighbouring carbon atoms of the aromatic ring form a six-membered aromatic ring;

and wherein $R^5$ and $R^6$ together with two neighbouring carbon atoms of the aromatic ring form a six-membered aromatic ring; and a solvent selected from the group consisting of water, buffer, and mixture of water and organic solvent miscible with water, wherein the water content is at least 50 vol. %;

b) Reaction of the aqueous solution of ions of at least two different rare-earth elements ($M^{3+}$) to be separated with the aqueous solution of the compound of general formula (I), at pH in the range of from 5 to 9, and a mixing time of at least 1 minute, to form at least one complex of the $M^{3+}$ ion with the compound of general formula (I) in the form of a precipitate or a crystalline phase; and c) Mechanical separation of the precipitate or of the crystalline phase from the reaction mixture using sedimentation, centrifugation, or filtration.

2. The method according to claim 1, wherein the molar ratio between the sum of rare-earth metal ions $M^{3+}$ and the compound of the general formula (I) is in the range of from 1:0.5 to 1:100.

3. The method according to claim 1, wherein the ions of at least two different rare-earth elements ($M^{3+}$) in the reaction mixture in step b) are in the form of their water-soluble salts with inorganic or organic acids.

4. The method according to claim 3, wherein the ions of at least two different rare-earth elements ($M^{3+}$) in the reaction mixture in step a) are selected from the group consisting of chloride, bromide, sulfate, nitrate, perchlorate, methansulfonate, trifluoromethansulfonate, formate, acetate, lactate, malate, citrate, 2-hydroxy isobutyrate, mandelate, diglycolate, and tartrate.

5. The method according to claim 1, wherein at least one additive is added into the reaction mixture in step b), wherein the additive is selected from the group comprising carboxylic acids consisting of from 1 to 11 carbon atoms, phosphinic acids comprising from 1 to 10 carbon atoms, phosphonic acids comprising from 1 to 10 carbon atoms, trifluoroacetic acid, 3-chlorobenzoic acid, chloride; dipicolinic acid, fluoride, glycine, glycolate, alpha-hydroxy-isobutyric acid, lactate, nitrate, phenylboronic acid, picolinic acid, pyridine, mandelic acid, salicylic acid, sulfate, thiocyanate, tributyl phosphate, dimethylsulfoxide, N,N-dimethylformamide, and N,N-dimethylacetamide.

6. The method according to claim 5, wherein the molar ratio between the sum of rare-earth metal ions and the additive in the reaction mixture of step a) is in the range of from 1:0.1 to 1:100.

7. The method according to claim 5, wherein the additive is selected from the group consisting of acetate, trifluoroacetic acid, benzoic acid, 3-chlorobenzoic acid, 2-methylbenzoic acid, 3-methylbenzoic acid, 4-methylbenzoic acid, chloride, citrate, dipicolinic acid, fluoride, formate, glycine, glycolate, oc-HIBA (alphahydroxyisobutyric acid), lactate, nitrate, phenylboronic acid, picolinic acid, pyridine, mandelic acid, salicylic acid, sulfate, thiocyanate, tributyl phosphate, dimethylsulfoxide, N,N-dimethylformamide, and N,N-dimethylacetamide.

8. The method according to claim 1, further comprising a step e) in which the reaction mixture from step c), after mechanical separation of the precipitate or of the crystalline phase, is subjected to evaporation, ultrafiltration, and/or ion-exchange chromatography, resulting in precipitation or crystallization of at least one complex of the $M^{3+}$ ion with the compound of general formula (I).

9. The method according to claim 1, further comprising:
- d) re-dissolving of the precipitate or of the crystalline phase from step c) in water, buffer, a mixture of water and organic solvent, which is miscible with water, or in aqueous solution of inorganic or organic acid.

10. The method according to claim 9, further comprising:
- e) pH adjustment of the solution from step d) to the pH value in the range of from 5 to 9, and repeating of steps b), c) and d).

11. The method according to claim 9, wherein the compound of the general formula (I) is separated from the reaction mixture after dissolving the precipitate or crystalline phase in step d).

12. The method according to claim 11, wherein the compound of the general formula (I) is separated from the reaction mixture using solid phase extraction, chromatography, or sorption on activated carbon.

13. A method for separation of rare-earth elements by precipitation, comprising:
- providing an aqueous solution comprising ions of at least two different rare-earth elements; and
- contacting the aqueous solution with a compound of general formula (I) to precipitate a complex of at least one of the at least two rare-earth elements with a compound selected from the group consisting of
- 2,2',2"-(10-benzyl-1,4,7,10-tetraazacyclododecane-1,4,7-triyl)triacetic acid;
- 2,2'-(4-(2-hydroxy-5-nitrobenzyl)-1,4,7,10-tetraazacyclododecane-1,7-diyl)diacetic acid;
- 2,2'-(4-(4-carboxybenzyl)-1,4,7,10-tetraazacyklododekane-1,7-diyl)diacetic acid; and
- 2,2',2"-(10-([1,1'-biphenyl]-4-ylmethyl)-1,4,7,10-tetraazacyclododecane-1,4,7-triyl)triacetic acid
- or with the compound of general formula (I), wherein the compound of general formula (I) has the following structure:

(I)

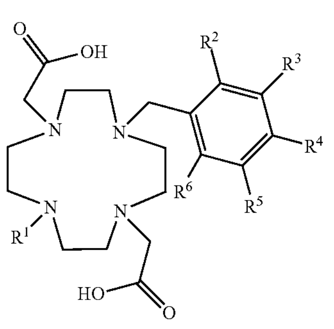

wherein
- $R^1$ is selected from the group consisting of H and $—CH_2COOH$;
- $R^2$, $R^3$, $R^4$, $R^5$ and $R^6$ are independently selected from the group consisting of —H, OH, $—NO_2$, —COOH, and phenyl;
- and wherein $R^2$ and $R^3$ together with two neighbouring carbon atoms of the aromatic ring form a six-membered aromatic ring;
- and/or $R^3$ and $R^4$ together with two neighbouring carbon atoms of the aromatic ring form a six-membered aromatic ring;
- and/or $R^4$ and $R^5$ together with two neighbouring carbon atoms of the aromatic ring form a six-membered aromatic ring;
- and/or $R^5$ and $R^6$ together with two neighbouring carbon atoms of the aromatic ring form a six-membered aromatic ring.

14. The method according to claim 13, wherein at most two of the substituents $R^2$, $R^3$, $R^4$, $R^5$ and $R^6$ of the compound of general formula (I) are other than H.

15. The method according to claim 13, wherein $R^2$ and $R^6$ of the compound of general formula (I) are independently H or OH.

16. The method according to claim 13, wherein $R^3$ and $R^4$ together with two neighbouring carbon atoms of the aromatic ring form a six-membered aromatic ring and at the same time $R^2$, $R^5$ and $R^6$ are H.

17. The method according to claim 13, wherein the group

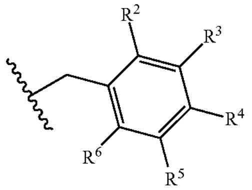

of the compound of general formula (I) is selected from the group comprising naphtalen-1-ylmethyl, and naphtalen-2-ylmethyl.

18. The method according to claim 13, wherein the compound is selected from the group consisting of:

2,2',2"-(10-benzyl-1,4,7,10-tetraazacyclododecane-1,4,7-triyl)triacetic acid;

2,2'-(4-(2-hydroxy-5-nitrobenzyl)-1,4,7,10-tetraazacyclododecane-1,7-diyl)diacetic acid;

2,2'-(4-(4-carboxybenzyl)-1,4,7,10-tetraazacyklododekane-1,7-diyl)diacetic acid;

2,2',2"-(10-(naphthalene-2-ylmethyl)-1,4,7,10-tetraazacyklododekane-1,4,7-triyl)triacetic acid;

2,2',2"-(10-(naphthalene-1-ylmethyl)-1,4,7,10-tetraazacyklododekane-1,4,7-triyl)triacetic acid;

and 2,2',2"-(10-([1,r-biphenyl]-4-ylmethyl)-1,4,7,10-tetraazacyclododecane-1,4,7-triyl)triacetic acid.

* * * * *